United States Patent
Nord et al.

(10) Patent No.: US 9,987,504 B2
(45) Date of Patent: Jun. 5, 2018

(54) PORTAL DOSIMETRY SYSTEMS, DEVICES, AND METHODS

(71) Applicant: Varian Medical Systems International AG, Zug (CH)

(72) Inventors: Janne Nord, Espoo (FI); Lasse Heikki Toimela, Espoo (FI)

(73) Assignee: VARIAN MEDICAL SYSTEMS INTERNATIONAL AG, Zug (CH)

( * ) Notice: Subject to any disclaimer, the term of this patent is extended or adjusted under 35 U.S.C. 154(b) by 491 days.

(21) Appl. No.: 14/677,392

(22) Filed: Apr. 2, 2015

(65) Prior Publication Data

US 2016/0287906 A1    Oct. 6, 2016

(51) Int. Cl.
 *A61N 5/10*    (2006.01)

(52) U.S. Cl.
 CPC .......... *A61N 5/1071* (2013.01); *A61N 5/103* (2013.01); *A61N 2005/1054* (2013.01)

(58) Field of Classification Search
 CPC ........ G11B 11/10515; G11B 11/10595; G11B 19/02; G11B 19/06; G11B 19/16; G11B 2020/10592; G11B 20/10527; G11B 2220/2529; G11B 7/005; G11B 7/09; A61N 5/1071; A61N 5/1031; A61N 5/1054; A61N 5/103; A61N 5/1064; A61N 2005/1072; A61N 5/1075; A61N 5/1047; A61N 2005/1076; A61N 2005/1087; A61N 2005/1074; A61N 5/1039; A61N 5/1043; A61N 5/1067; A61N 2005/1095; A61N 2005/1054; A61N 5/1049; A61N 2005/1091; A61N 2005/1061; A61N 5/1042; A61N 5/1037; A61N 5/10; A61N 5/1048; A61N 5/1045; A61N 5/1017; A61N 2005/105; A61N 5/1065
 USPC ............................... 378/64, 65, 97
 See application file for complete search history.

(56) References Cited

U.S. PATENT DOCUMENTS

| | | | |
|---|---|---|---|
| 7,945,022 B2 | 5/2011 | Nelms et al. | |
| 2002/0080915 A1* | 6/2002 | Frohlich | A61N 5/103 378/65 |
| 2007/0041497 A1 | 2/2007 | Schnarr et al. | |
| 2007/0195930 A1 | 8/2007 | Kapatoes et al. | |
| 2008/0298550 A1* | 12/2008 | Otto | A61N 5/103 378/65 |
| 2009/0147916 A1* | 6/2009 | Fallone | A61N 5/103 378/65 |
| 2012/0230462 A1* | 9/2012 | Robar | A61N 5/1049 378/4 |
| 2012/0250971 A1 | 10/2012 | Holmes et al. | |

(Continued)

OTHER PUBLICATIONS

Wendling et al., "A fast algorithm for gamma evaluation in 3D", Medical Physics, AIP, Melville, NY, US, vol. 34, No. 5, Apr. 19, 2007, pp. 1647-1654.

(Continued)

*Primary Examiner* — Irakli Kiknadze
(74) *Attorney, Agent, or Firm* — Shapiro, Gabor and Rosenberger, PLLC

(57) ABSTRACT

Systems, devices, and methods for dosimetric verification of radiation therapy treatments by selective evaluation of measurement points. Systems, methods, and computer program-products for providing dosimetric verification of radiation therapy treatments by evaluating measurement points using different evaluation criteria.

45 Claims, 7 Drawing Sheets

(56) References Cited

U.S. PATENT DOCUMENTS

2012/0305793 A1 12/2012 Schiefer
2013/0085735 A1 4/2013 Vilsmeier
2014/0105355 A1 4/2014 Toimela et al.

OTHER PUBLICATIONS

Extended European Search Report dated Aug. 16, 2016, in European Application No. 16163147.8.
European Examination Report dated May 15, 2017, in European Application No. 16163147.8.
Van Elmpt et al., "A Monte Carlo based three-dimensional dose reconstruction method derived from portal dose images," Med. Phys. vol. 33, No. 7, Jul. 2006, pp. 2426-2434.
Yu, "Intensity Modulated Are Therapy: Technology and Clinical Implementation," University of Maryland School of Medicine, Jun. 30, 2014 (downloaded).
Sharma et al., "Portal dosimetry for pretreatment verification of IMRT plan: a comparison with 2D ion chamber array," Journal of Applied Clinical Medical Physics, vol. 11, No. 4, Fall 2010, pp. 238-248.
Arridge et al., "Optical tomography: forward and inverse problems," arXiv:0907.2586v1 [math.AP] Jul. 15, 2009.
Ren, "Recent Developments in Numerical Techniques for Transport-Based Medical Imaging Methods," Commun. Comput. Phys., vol. 8, No. 1, pp. 1-50, Jul. 2010.
Cilla et al., "Comparison of measured and computed portal dose for IMRT treatment," Journal of Applied Clinical Medical Physics, vol. 7, No. 3, Summer 2006, pp. 65-79.
Tang et al., "Comparing Radiation Treatments Using Intensity-Modulated Beams, Multiple Arcs and Single Arc," Int J Radiat Oncol Bio Phys, Apr. 2010, 76(5), 1554-1562.
J. Godart et al., "Reconstruction of high-resolution 3D dose from matrix measurements: error detection capability of the COMPASS correction kernel method," Phys. Med. Biol. vol. 56 (2011), pp. 5029-5043.
Olch, "Evaluation of the accuracy of 3DVH software estimates of dose to virtual ion chamber and film in composite IMRT QA," Journal of Applied Clinical Medical Physics, vol. 11, No. 4, Fall 2010, pp. 81-86.
Webb, "Volumetric-modulated arc therapy: its role in radiation therapy," Medical Physics Web, Jun. 25, 2009.
Wang et al., "Arc-modulated radiation therapy (AMRT): a single-arc form of intensity-modulated arc therapy," Phys. Med. Biol. vol. 53 (2008), pp. 6291-6303.
Karin W. Lamberts et al., "Qualitative determination of errors causing portal dose differences using gamma evaluation parameters," Medical Engineering Technische Universiteit Eindhoven, Aug. 2005, Course Code: 8Z150.
Van Elmpt et al., "A literature review of electronic portal imaging for radiotherapy dosimetry," Radiotherapy and Oncology, vol. 88 (1008), pp. 289-309.
Vieira, "Dosimetric Verification of Intensity Modulated Radiotherapy with an Electronic Portal Imaging Device," Department of Radiation Oncology, Division of Medical Physics, Erasmus MC/Daniel den Hoed Cancer Center, Groene Hilledijk 301, 3075 EA Rotterdam, The Netherlands, Jun. 30, 2014 (downloaded).
Low et al., "A technique for the quantitative evaluation of dose distributions," Medical Physics, vol. 25, No. 5, May 1998, pp. 656-661.
Wendling et al: "A fast algorithm for gamma evaluation in 3D," Medical Physics, AIP, Melville, NY, US, vol. 34, No. 5, Apr. 19, 2007, pp. 1647-1654, XP012103402, Section II. Materials and Methods.
Yuan Jiankui et al: "A $\gamma$ dose distribution evaluation technique using the k-d tree for nearest neighbor searching," Medical Physics, AIP, Melville, NY, US, vol. 37, No. 9, Aug. 20, 2010, pp. 4868-4873, XP0121449959, Section II. Methods and Materials.
International Search Report and Written Opinion for International Application No. PCT/EP2013/070797, dated Nov. 19, 2013.
Williams, "IMRT: delivery techniques and quality assurance", The British Journal of radiology, 76 (2003), 766-776.
Winiecki et al., "The gamma evaluation method as a routine QA procedure of IMRT", Rep. Pract. Oncol. Radiother., 2009 14/5, 162-168.
Bailey et al. ,"EPID dosimetry for pretreatment quality assurance with two commercial systems", Journal of Applied Clinical Medical Physics, vol. 3, No. 4, 2012.
Fuangrod et al., "Development of EPID-based Real Time Dose Verification for Dynamic IMRT", World Academy of Science, Engineering and Technology, 56, 2011.
Fuangrod et al., "A system for EPID-based real-time treatment delivery verification during dynamic IMRT treatment", Med. Phys. 40 (9), Sep. 2013.
Nijsten et al. "A global calibration model for s-Si EPIDs used for transit dosimetry", Med. Phys. 34 (10), Oct. 2007.
Rowshanfarzad et al., "Measurement and modeling of the effect of support arm backscatter on dosimetry with a Varian EPID", Med. Phys. 37 (5), May 2010.
Van Esch et al: "The use of an aSi-based EPID for routine absolute dosimetric pre-treatment verification of dynamic IMRT fields," Radiotherapy and Oncology, vol. 71, No. 2, May 2004, pp. 223-234, XP055087412, Section 2.1. The aSi-based EPID for dosimetry in dynamic mode.
Tyler et al., "Clinical validation of an in-house EPID dosimetry system for IMRT QA at the Prince of Wales Hospital," Journal of Physics: Conference Series 444 (2013) 012043.
Van Esch et al., "Optimized Varian aSi portal dosimetry: development of datasets for collective use," Journal of Applied Clinical Medical Physics, vol. 14, No. 6, 2013, pp. 82-99.
Wendling et al., "A simple backprojection algorithm for 3D in vivo EPID dosimetry of IMRT treatments," Med. Phys. vol. 36, No. 7, Jul. 2009, pp. 3310-3321.
Sattarivand et al., "Effects of ROI Placement on PET-Based Assessment of Tumor Response to Therapy," International Journal of Molecular Imaging, vol. 2013 (2013), Article ID 132804.
Tam et al., "Reducing excess radiation from portal imaging of pediatric brain tumors," Journal of Applied Clinical Medical Physics, vol. 14, No. 5, 2013.
Court et al., "Experimental evaluation of the accuracy of skin dose calculation for a commercial treatment planning system," Journal of Applied Clinical Medical Physics, vol. 9, No. 1, 2008, pp. 29-35.
Shiau et al., "Left-Sided Whole Breast Irradiation with Hybrid-IMRT and Helical Tomotherapy Domestic Comparison," BioMed Research International, vol. 2014 (2014), Article ID 741326.
Depuydt et al., "A quantitative evaluation of IMRT dose distributions: refinement and clinical assessment of the gamma evaluation," Radiotherapy and Oncology, vol. 62, 2002, pp. 309-319.
European Examination Report dated Mar. 9, 2018, in European Application No. 16163147.8.

* cited by examiner

PORTAL DOSIMETRY SYSTEMS, DEVICES, AND METHODS

FIELD

The present disclosure relates generally to delivering radiation to a patient, and more particularly to systems, methods, and computer program products for providing dosimetric verification of radiation therapy treatments by selective evaluation of measurement points. The present disclosure also relates to systems, methods, and computer program-products for providing dosimetric verification of radiation therapy treatments by evaluating measurement points using different evaluation criteria. The present disclosure also relates to systems, methods, and computer program products for performing quality control measurements prior to and during radiation treatment.

BACKGROUND

In general, radiosurgery and radiotherapy treatments consist of several phases. First, a precise three-dimensional (3D) map of the anatomical structures in the area of interest (head, body, etc.) is constructed to determine the exact coordinates of the target within the anatomical structure, namely, to locate the tumor or abnormality within the body and define its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. The third phase is where the radiation treatment plan is executed. During this phase, the radiation dose is delivered to the patient according to the prescribed treatment plan using radiation treatment techniques, such as intensity-modulated radiation therapy (IMRT) and volumetric modulated arc therapy (VMAT), for example. These techniques are typically used with a radiotherapy system, such as a linear accelerator (linac), equipped with a multileaf collimator (MLC) to treat pathological anatomies (tumors, lesions, vascular malformations, nerve disorders, etc.) by delivering prescribed doses of radiation (X-rays, gamma rays, electrons, protons, and/or ions) to the pathological anatomy while minimizing radiation exposure to the surrounding tissue and critical anatomical structures.

There are many factors that can contribute to differences between the prescribed radiation dose distribution and the actual dose delivered (i.e., the actual dose delivered to the target during the radiation treatment). One such factor is uncertainty in the patient's position in the radiation therapy system. Other factors involve uncertainty that is introduced by changes that can occur during the course of the patient's treatment. Such changes can include random errors, such as small differences in a patient's setup position. Other sources are attributable to physiological changes that might occur if a patient's tumor regresses or if the patient loses weight during therapy. Another category of uncertainty includes motion. Motion can potentially overlap with either of the categories as some motion might be more random and unpredictable, whereas other motion can be more regular. Many other sources of uncertainties exist, such as, missing bolus or fixation device (human error), wrong patient, mechanical failure/calibration error/changes is radiation output, corrupted data (plan is not consistent with calculated dose), wrong delivery machine (patient may be treated on another delivery machine in case the original is not functional at the moment, for example. These uncertainties can affect the quality of a patient's treatment and the actual radiation dose delivered to the target.

The accuracy in delivering a predicted radiation dose to a target based on a predetermined treatment plan, therefore, plays an important role in the ultimate success or failure of the radiation treatment. Inaccurate dose delivery can result in either insufficient radiation for cure, or excessive radiation to nearby healthy tissue and organs at risk (OARs). A radiation dose that is too high may cause serious damage to healthy tissues surrounding the tumor as well as organs located nearby, whereas a dose that is too low may jeopardize the probability of cure. Therefore, a relatively small error in the delivered radiation dose may seriously harm the patient. Quality assurance tools and protocols are therefore needed to verify that the prescribed radiation dose is delivered to the target without jeopardizing the organs at risk and the healthy tissue.

Because of the high complexity and uniqueness of treatment plans, patient-specific pre-treatment (i.e., without the patient in the beam) verification is generally considered a necessary prerequisite to patient treatment. Pre-treatment verification includes procedures to compare the whole or at least part of the intended treatment plan with measurements of corresponding radiation beams delivered by the linear accelerator (linac) outside the patient treatment time.

Dosimetric verification is one of the pre-treatment protocols implemented for radiation therapy treatments. Dosimetric verification includes verification that the dose distribution delivered is in fact the dose distribution predicted to be delivered to the patient. Because of the increased beam delivery complexity offered by some of the radiation therapies, such as (IMRT) and (VMAT) treatments, dosimetric verification for treatments require rigorous verification of the radiation dose delivery.

In established dose verification methods, integrated dose distribution images are compared against dose images predicted by the treatment planning system (TPS) using a gamma evaluation method. The gamma evaluation method is widely used in dose measurements, because it combines spatial errors and dose level errors in a single value. The weakness of such an evaluation, however, is that all measurements points are evaluated based on the same criteria, even though the evaluation criteria may be too loose or too rigorous for certain points. A loose evaluation criteria may validate dose delivery even though the detected dose discrepancies may be too high for an organ at risk (overdose or hotspot generated in an organ at risk is much more severe than an overdose or hotspot in the target or a healthy tissue, for example), whereas a stricter evaluation criteria may reject dose delivery even though the detected dose discrepancies do not affect the patient.

Further, in established dose verification methods, if the measured radiation is different from the expected radiation, the treatment is stopped. However, if the radiation beam is tangential to the patient, a small change in the patient outline can make a significant difference in the measured dose while the actual dose in the patient is not affected significantly. In fact, in some instances, the radiation field is made intentionally larger than the target. In arc therapy treatments, for example, tangential fields are more likely to occur because all radiation directions in the plane are used. Thus, when all of the points irradiated by the beam are used in real-time evaluation of the treatment, the established dose evaluation methods may falsely detect a dose error and trigger stopping of the radiation treatment.

SUMMARY

The present disclosure provides systems, methods, devices, and computer program products for radiation pre-treatment, treatment, and in-vivo dosimetry verification. The dosimetry verification includes evaluating dose distribution using different evaluation criteria for different points in the measurement plane.

The present disclosure also provides systems, methods, and computer program products for evaluating dose distribution using different gamma criteria for different points in the measurement plane. Each point in the measurement plane can be associated with a corresponding gamma criteria. The values for the different gamma criterias can be defined based on the type of anatomical structures that project onto the points in the measurement plane.

The present disclosure also provides systems, methods, and computer program products for selectively evaluating points in the measurement plane. The selective evaluation excludes points that are irradiated by radiation beams that do not intersect in the patient and/or radiation beams that travel near the surface of the patient and/or radiation beams that penetrate the surface of the patient at the depth of approximately 1 cm from being evaluated. The evaluation can include evaluating the selected points using a gamma criteria. The evaluation can also include evaluating the selected points using different gamma criterias.

The present disclosure provides systems, methods, and computer program products for electronic portal imaging device (EPID)-based pre-treatment dose verification for treatment plans.

The present disclosure also provides systems, methods, devices, and computer program products for real-time radiation dose verification using electronic portal imaging devices (EPIDs), wherein only selected points within the measurement plane are used for treatment verification.

The present disclosure also provides an (EPID) calibration model for converting measured dose distributions into absolute dose distributions.

The present disclosure also provides systems, methods, and computer program products for quantitative evaluation of dose distributions.

The present disclosure also provides a non-transitory computer-readable storage medium upon which is embodied a sequence of programmed instructions for quality control in a radiation therapy treatment system as disclosed herein, including a computer processing system, as disclosed herein, which executes the sequence of programmed instructions embodied on the computer-readable storage medium to cause the computer processing system to perform the steps of the methods as disclosed herein.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

DETAILED DESCRIPTION

To verify that a radiation treatment procedure is correctly applied, quality assurance protocols for dosimetric verification of the treatment plan, as well as in-vivo dosimetry can be implemented at corresponding stages of the radiation therapy. Quality assurance protocols are implemented to verify that the developed treatment plan is accurate, the treatment delivery is accurate, and that the actual dose delivered to the patient is the planned dose. Quality assurance is especially needed in advanced radiotherapy techniques, such as, intensity-modulated radiotherapy (IMRT) or arc therapy, where in order to concentrate the dose inside the tumor while sparing the organs at risk (OARs), the treatment plan often has a high gradient dose distribution.

Treatment execution verification can include two steps. A first step involves pre-treatment measurements and a second step involves during or in-treatment measurements. The pre-treatment measurements are performed to check the proper transfer of treatment parameters from the planning phase to the specific radiation treatment device prior to the first treatment of the patient. It also ensures that the execution of the treatment plan by the device is correct. Pre-treatment verification is thus a procedure comparing the whole or at least part of the intended treatment plan with measurements of corresponding radiation beams delivered by a linear accelerator outside the patient treatment time, namely, with open fields or a phantom. This comparison focuses on predicted and measured leaf positions, dose delivered to the detector or phantom, or incident energy fluence extracted for measurements.

The during (or "in") treatment verification is a procedure that focuses on comparing all or part of the planned and the delivered dose distribution based on measurements acquired during treatment of the patient. These measurements can then be used to determine the dose delivered to the detector or patient, or incident energy fluence obtained from measurements.

Figure 1:
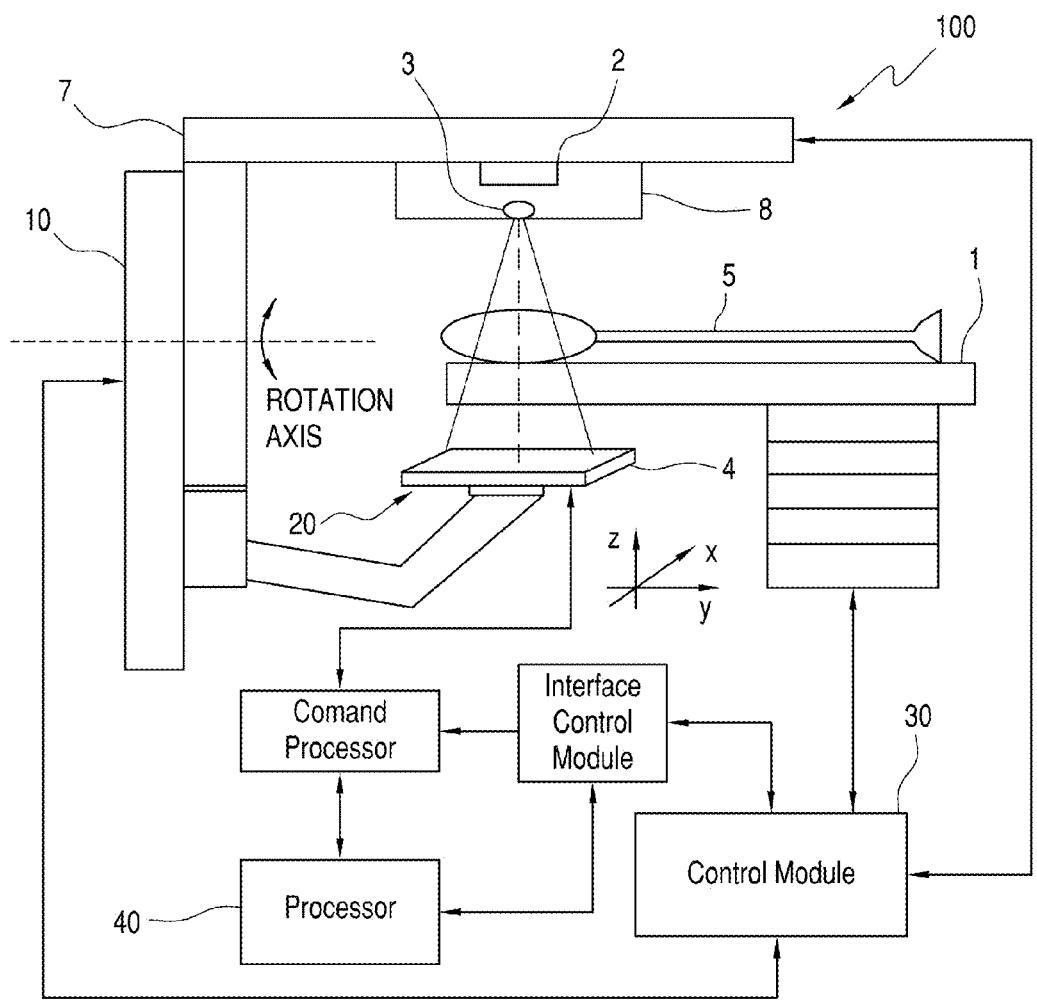
FIG. 1 is a perspective view of a radiation therapy system according to various embodiments of the invention.

FIG. 1 illustrates an exemplary radiation therapy treatment system 100 that can provide radiation therapy to a patient 5 positioned on a treatment couch 1, and allow for the implementation of various pre-treatment and in-treatment portal dosimetry verifications for quality assurance (QA) protocols. The radiation therapy treatment can include photon-based radiation therapy, particle therapy, electron beam therapy, or any other type of treatment therapy. In an embodiment, the radiation therapy treatment system 100 includes a radiation treatment device 10, such as, but not limited to, a radiotherapy or radiosurgery device, which can include a gantry 7 supporting a radiation module 8 which includes one or more radiation sources 3 and a linear accelerator (linac) 2 operable to generate a beam of kV or MV X-ray radiation. The gantry 7 can be a ring gantry (i.e., it extends through a full 360 degree arc to create a complete ring or circle), but other types of mounting arrangements may also be employed. For example, a static beam, or a C-type, partial ring gantry, or robotic arm could be used. Any other framework capable of positioning the radiation module 8 at various rotational and/or axial positions relative to the patient 5 may also be used.

The radiation module 8 can also include a modulation device (not shown) operable to modulate the radiation beam as well as to direct a therapeutic radiation beam toward the patient 5 and toward a portion of the patient which is desired to be irradiated. The portion desired to be irradiated is referred to as the target or target region or a region of interest. The patient 5 may have one or more regions of interest that need to be irradiated. A collimation device (not shown) may be included in the modulation device to define and adjust the size of an aperture through which the radiation beam may pass from the source 3 toward the patient 5. The collimation device may be controlled by an actuator (not shown) which can be controlled by a computer processing system 40 and/or a controller 30.

In an embodiment, the radiation therapy device is a kV or MV energy intensity modulated radiotherapy (IMRT) device. The intensity profiles in such a system are tailored to the treatment requirements of the individual patient. The intensity modulated radiotherapy fields are delivered with a multi-leaf collimator (MLC), which can be a computer-controlled mechanical beam shaping device attached to the head of the linear accelerator and includes an assembly of metal fingers or leaves. The (MLC) can be made of 120 movable leaves with 0.5 and/or 1.0 cm leaf width, for example. For each beam direction, the optimized intensity profile is realized by sequential delivery of various subfields with optimized shapes and weights. From one subfield to the next, the leaves may move with the radiation beam on (i.e., dynamic multileaf collimation (DMLC)) or with the radiation beam off (i.e., segmented multileaf collimation (SMLC).

The device 10 can also be a tomotherapy device where intensity modulation is achieved with a binary collimator which opens and closes under computer control. As the gantry continuously rotates around the patient, the exposure time of a small width of the beam can be adjusted with the opening and closing of the binary collimator, allowing the radiation to be delivered to the tumor through the most preferred directions and locations of the patient.

The device 10 can also be a helical tomotherapy device which includes a slip-ring rotating gantry. The device 10 can also be an intensity modulated arc therapy device (IMAT) where instead of using rotating fan beams, rotational cone beams of varying shapes are used to achieve intensity modulation. The device 10 can also be a simplified intensity modulated arc therapy (SIMAT) device which uses multiple arcs, or a sweeping window arc therapy device (SWAT), where the (MLC) leaf positions sweep across the target planning volume (TPV) with rotation. The device 10 can also be a volumetric modulated arc therapy (VMAT) device where dose rate, beam aperture shape, and the speed of rotation can be continuously varied to deliver the prescribed dose to the target planning volume (TPV).

The device 10 further includes a portal dose imaging device 20 for acquiring digital images to be used for portal dosimetry verification. The portal dose imaging device 20 can be an electronic portal imaging device (EPID). The portal dose imaging device 20 can be placed at different locations, such as, on top of the treatment couch 1, or attached to the accelerator head 2, for example. The portal dose imaging device 20 can generate immediate 2D digital information. It can be a camera-based device, such as a camera-based (EPID), or an amorphous silicon based device, such as an amorphous silicon (EPID). The (EPID) 20 can also be a CCD-camera based (EPID), which is effectively an array of simultaneously integrating dosimeters with a dead time in between acquired frames of about 0.1 ms, for example. Another alternative is a flat panel imager (or amorphous silicon EPID), which offers good image quality, high optical transfer efficiency, large imaging area, and resistance to radiation.

An exemplary amorphous silicon imaging device that can be used is a aSi1000 EPID imager that has arrays of light sensitive amorphous-Si photodiodes arranged in 40×30 $cm^2$ active detector area 4 and has a maximum frame rate of 9.574 fps, each frame being a scan of the detector elements. The flat panel imager generally consists of picture elements (pixels) that register the amount of radiation that falls on them and convert the received amount of radiation into a corresponding number of electrons. The electrons are converted into electrical signals which are further processed using either the imaging device 20 or a computer 40. Such a configuration (i.e., digital imaging detector(s) positioned opposite the therapeutic source(s)) provides the ability to continuously and immediately capture the energy and intensity of the therapeutic radiation transmitted from each arc field segment and/or during a continuous arc beam delivery, in order to generate two-dimensional (2D) images of digitized X-ray measurements. Because the portal dose imaging device 20 generates immediate, 2D digital information, it facilitates 2D dosimetry at any gantry angle.

The computer 40 includes typical hardware such as a processor, and an operating system for running various software programs and/or communication applications. The computer can include software programs that operate to communicate with the radiation therapy device 10, and the software programs are also operable to receive data from any external software programs and hardware. The computer 40 can also include any suitable input/output devices adapted to be accessed by medical personnel, as well as I/O interfaces, storage devices, memory, keyboard, mouse, monitor, printers, scanner, etc. The computer 40 can also be networked with other computers and radiation therapy systems. Both the radiation therapy device 10 and the computer 40 can communicate with a network as well as a database and servers. The computer 40 is also adapted to transfer medical image related data between different pieces of medical equipment.

The system 100 can also include a plurality of modules containing programmed instructions which communicate with each other and cause the system 100 to perform different functions related to radiation therapy/surgery, as discussed herein, when executed. For example, the system 100 can include a treatment plan module operable to generate the treatment plan for the patient 5 based on a plurality of data input to the system by the medical personnel, the treatment plan including a predicted radiation dose distribution, a patient positioning module operable to position and align the patient 5 with respect to the isocenter of the gantry 7 for a particular radiation therapy treatment, an image acquiring module operable to instruct the radiation therapy device 10 to acquire images of the patient 5 prior to the radiation therapy treatment and/or during the radiation therapy treatment (i.e., in-vivo images), and/or to instruct other imaging devices or systems to acquire images of the patient 5.

The system 100 can further include a treatment delivery module operable to instruct the radiation therapy device 10 to deliver the treatment plan with or without the patient 5 in place, a converting module operable to convert the 2D portal images (EPIs) into 2D portal doses, an analysis module operable to compute comparisons between predicted and measured dose distributions, a selection module operable to select measurement points for dose evaluation based on a selection criteria, an evaluation module to evaluate measurement points for dose discrepancies based on different evaluation criteria applicable to different points, a calculation module operable to calculate dose delivery errors, and an execution module operable to initialize stopping the radiation process, sending an alert signal to the physician, or initiate an alarm procedure. The modules can be written in the C or C++ programming languages, for example. Computer program code for carrying out operations of the invention as described herein may also be written in other programming languages.

As part of the quality control protocol, for pre-treatment portal dosimetry verification, the radiation dose distribution delivered by the treatment fields is validated before starting the patient treatment. Patient treatment involves irradiating the patient with treatment beams (i.e., X-rays, for example) according to a prescribed delivery treatment plan.

The prescribed delivery plan is developed using a treatment planning system (TPS) prior to the treatment phase, and involves developing a plan using special computer software to optimally irradiate the tumor and minimize dose to the surrounding normal tissue from different angles and planes. First, a precise three-dimensional (3D) map of the anatomical structures in the area of interest (head, body, etc.) is constructed using any one of a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. For example, in order to obtain CT images, a motorized table moves the patient through the circular opening in a CT imaging system. As the patient passes through the CT imaging system, a source of x-rays rotates around the inside of the circular opening. A single rotation takes about 1 second. The x-ray source produces a narrow, fan-shaped beam of x-rays used to irradiate a section of the patient's body. The thickness of the fan beam may be as small as 1 millimeter or as large as 10 millimeters. In typical examinations there are several phases, each made up of 10 to 50 rotations of the x-ray tube around the patient in coordination with the table moving through the circular opening. The patient may receive an injection of a contrast material to facilitate visualization of vascular structure.

One or more detectors, such as an EPID, on the exit side of the patient record the x-rays exiting the section of the patient's body being irradiated as an x-ray "snapshot" at one position (angle) of the source of x-rays. Many different "snapshots" (angles) are collected during one complete rotation. The data is then sent to a computer to reconstruct all of the individual "snapshots" into a cross-sectional image (slice) of the internal organs and tissues for each complete rotation of the source of x-rays. The CT images can be calculated from the absorption signals detected with the detectors while the source and the detector circle around the patient by back projection. To do so, the intensity of the detected signals are projected back from the detector to the source and overlayed in the area of the x-rayed object.

Figure 2:
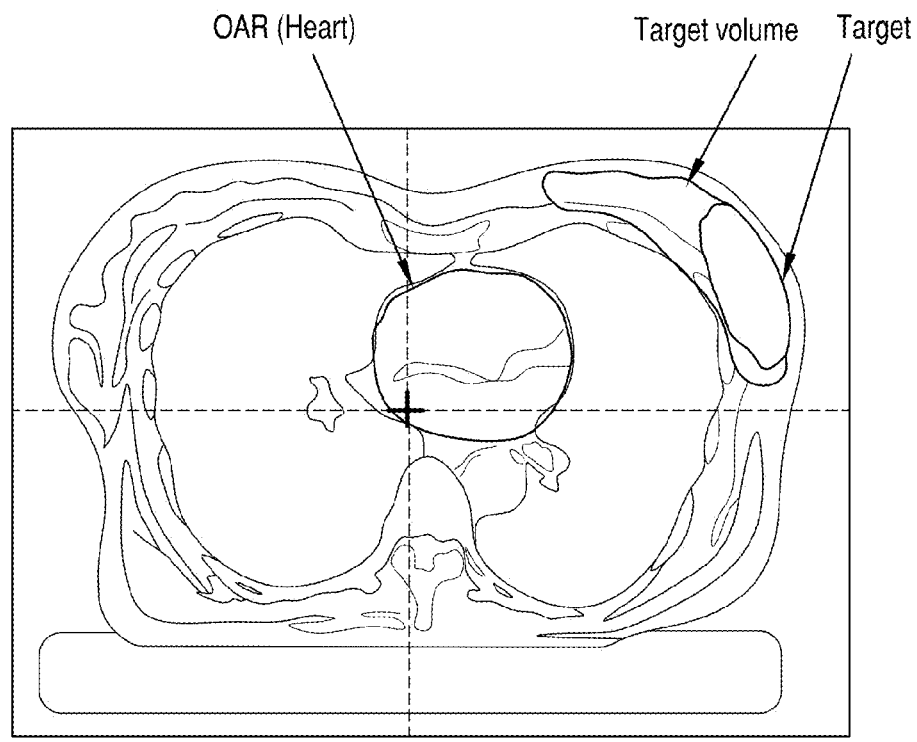
FIG. 2 illustrates target volume definition according to various embodiments.

Treatment planning is based on anatomical characteristics of the individual patient. Anatomical characteristics include the external geometry, the localization, and the extent of the tumor and organs at risk as well as variation in the tissue density. The anatomical description (i.e., anatomical model) can be derived from the set of CT images (or MRI, SPECT, PET, etc.), for example, but a set of contours in combination with simulator images may also be used. Based on the CT images and/or contours, the anatomical structures, namely, points, contours, and volumes that specify the patient anatomy in the TPS, are generated, as shown in FIG. 2. Each anatomical description is uniquely linked to one or more beam arrangements.

Then, a motion path for the radiation beam is computed to deliver a dose distribution that the surgeon finds acceptable, taking into account a variety of medical constraints, including the locations and types of organs at risk (OARs). An OAR is a critical structure located close to the target for which the dose of radiation must be severely constrained. Overdosing a critical structure with radiation may lead to medical complications. OARs are also termed as "sensitive structures" or "critical structures". During this phase, a team of specialists develop a treatment plan using special computer software to optimally irradiate the tumor and minimize dose to the surrounding normal tissue and OARs, by designing beams of radiation to converge on the target area from different angles and planes. The treatment plan includes a trajectory (motion path) for the radiation beam computed to deliver a dose distribution that the treating physician finds acceptable. The beam trajectory is developed based on knowledge of the exact coordinates of the target within the anatomical structure, the exact coordinates of the OARs, which are adjacent the target, the coordinates of the OARs which are not immediately adjacent the target, but to which even a small amount of dose would be detrimental, and the exact shape and size of the tumor or abnormality within the body.

The goals of radiation treatment planning include homogeneity, conformity, avoidance, and simplicity. A homogeneity requirement is to irradiate the tumor volume within the specified dose levels. It is important for a treatment plan to have uniform dose distribution on the target so that "cold spots" can be minimized. A "cold spot" is a portion of a structure, such as an organ, a tumor, or a tissue, for example, that receives under its required dose level. On the other hand, the term "hot spot" is used to denote a portion of a structure that receives more than the desired dose level. A conformity requirement is used to achieve the target dose control while minimizing damage to OARs or healthy, normal tissue. An avoidance requirement can be to limit the dose delivered to OARs. A simplicity requirement is to provide a treatment plan as simple as possible. Simple treatment plans typically reduce the treatment time as well as implementation error. In optimizing the treatment plan, a three-dimensional volume of a region of interest can be represented by a grid of voxels, and the treatment plan can include the desired dose distribution to each voxel from the radiation source. The treatment plan can also include the set of organ geometries that are of interest to the physician and the desired dose levels for each organ of interest.

To optimize arc delivery treatment plans (for arc therapy, a trajectory may be an arc, typically a single 360 degree, or a single 180 degree revolution, formed by the rotation of the treatment gantry about the patient), at the outset of the treatment planning process, a number of control points along the trajectory can be specified. Each control point is associated with a set of treatment parameters, including but not limited to, a set of (MLC) leaf positions, (MLC) shape, gantry rotation speed, gantry position, dose rate, and/or any other parameters. The number and position of the control points may be set in any convenient manner, such as, but not limited to, by using the treatment planning software, or by the system operator. In an exemplary embodiment, the trajectory can include a single 180 degree arc trajectory and approximately 177 sequential control points, which means that there are 177 configurations that the linac (2) should conform to in order to deliver the planned treatment. Based on the treatment parameters, a dose distribution within the treatment volume is calculated for each control point by any number of techniques, such as, but not limited to, pencil beam convolution, or any other suitable algorithm. The dose distributions are calculated using the actual portal imaging parameters including field size, the CIAO (completely irradiated aperture outline) aperture, total number of monitor units (MUs), gantry angle, collimator angle, couch angle, and energy.

Once the treatment plan is completed, the patient's OAR and target geometry as well as the treatment plan parameters are stored in a database of computer 40 for future use. The information stored in the database could serve as a basis for a knowledge-based planning model. The knowledge-based model contains dose and volume information for a certain type of patient. The relationship between volume and dose in this patient can then be applied for future cases. The knowledge-based model enables clinicians to use the dose and patient anatomy information from the database to estimate the dose distribution in new patients, as well as to reflect preferred treatment methodologies and protocols.

Alternatively, the treatment plan for the current patient could be generated based on a previously generated knowledge-based model by using the patient's OAR and target geometry and a database of previously planned similar patients.

Once the treatment plan is completed, the radiation dose distribution for each segment is associated with the corresponding gantry angle, (MLC) configuration, and monitor unit (MU) extracted from the system's RTPLAN file. The RTPLAN is a treatment planning module that can include a plurality of radiotherapy (RT) modules associated with the processor 40 that work together to address the requirements for transfer of treatment plans before or during a course of treatment (i.e., in-treatment). The modules can include information about the general treatment plan, prescription, tolerance tables, patient setup, fraction scheme, beams, etc. By extracting the gantry angle, (MLC) configuration, and the monitor unit (MU) for each control point from the RTPLAN file and associating the extracted parameters with the corresponding calculated dose distributions for each segment, a predicted portal dose image for each segment/field can be generated.

Various methods can be applied to generate the predicted portal dose images, namely, the predicted portal dose images for the arc segments located between consecutive control points. For example, a previously determined portal dose image prediction (PDIP) algorithm, such as the one commercially adopted for Varian systems, could be used to calculate the predicted dose images based on the theoretical TPS photon intensity matrix, the main collimator positions, and the total monitor units (MUs). Alternatively, an EPID dose prediction model which is based on the energy fluence model used in a Pinnacle TSP can also be used to generate the predicted images. In yet another embodiment, the predicted images can be generated based on a prediction algorithm derived from the obtained CT images. In such a case, the patient geometry as observed in the planning CT scan is converted into an equivalent homogeneous phantom, and a limited set of EPID measurements are executed to derive the input parameters of this model. The derived model is then saved for future use. In an alternative embodiment, the predicted images are generated based on a prediction algorithm which uses as parameters data based on the planning CT scan of the patient and on the irradiation geometry as determined in the treatment planning process. In yet another embodiment, a fluence based prediction model could be used which utilizes Monte Carlo simulation and linac-specific engineering schematics of the MLCs to create the prediction model. The energy fluence is converted to dose using a superposition of EPID-specific dose kernels. Scatter from the patient or phantom is approximated using Monte Carlo calculated scatter fluence kernels. The prediction model is again saved for future use. In yet another embodiment, a portal dose image prediction (PDIP) software such as the one used in the Varian Eclipse treatment planning system can also be used to generate the predicted images. In yet another embodiment, the prediction algorithm as described in "Optimized Varian aSi portal dosimetry: development of datasets for collective use", by Van Esch et al., incorporated herein by reference in its entirety, can be used to generate the predicted portal dose images. Any other prediction algorithms could be used to generate the predicted portal dose images. The algorithm and associated data, namely, the irradiation geometry, irradiation fields, and irradiation energies could also be assembled in a dataset for later use.

By generating a predicted dose image for each segment/field, a sequence of 2D predicted portal dose images are obtained. The various segments for a single beam can be integrated into a single 2D digital image per beam (i.e., per gantry angle). The generated sequence of predicted portal dose images can be stored in the computer processor 40.

For IMRT, the MLC is used to shape the radiation beam into multiple segments per beam angle, creating fluence maps of varying intensity. Upon delivery, the fluence-modulated beams sum in three dimension (3D) to create a highly conformal dose distribution. This technique increases the ability to cover tumor targets of irregular shape with the prescription dose while sparing nearby normal tissue and organs at risk. In order to create these conformal dose distributions, IMRT utilizes a technique of breaking up a large beam into a grid of several smaller beams known as "beamlets", and the beamlets are given an intensity weight between 0% and 100% of the total beam intensity. The beamlets are then combined to create a pattern of intensities known as the intensity map, which represents the radiation output from the specific angle of incidence of that beam required to deliver dose to the target and spare other tissues. This process is carried out for each of the beams used in the IMRT treatment plan and all intensity maps are then summed in 3D to create the desired dose distribution. Intensity maps are translated into deliverable MLC configurations, known as segments, for each beam. The IMRT treatments can then be delivered in a step-and-shoot method, during which the radiation beam is off between segments, or with a dynamic method, during which the radiation beam remains on while the MLC form the different segment.

After the treatment planning, the treatment plan, including the CT image set including the 3D image of the patient in the treatment position, the anatomical characteristics, such as the external geometry, the localization, and the extent of the tumor and organs at risk, as well as variation in the tissue density, and the associated anatomical structures, namely, points, contours, and volumes that specify the patient anatomy in the TPS is exported in DICOM-RT.

After the treatment planning and before treatment delivery, the pre-treatment dose validation described herein is executed as part of the quality assurance protocol. The dosimetry methods for verification (for both the pre-treatment and in-treatment verification) can include: non-transmission dosimetry, which includes a determination of the dose in the detector, patient, or phantom, or a determination of the incident energy fluence based on measurements without an attenuating medium between the source of radiation and the detector (i.e., phantom or patient); transmission dosimetry, which includes a determination of the dose at the position of the detector, patient or phantom, or determination of the incident energy fluence based on radiation transmitted through the patient or phantom; in-phantom dosimetry, which includes a determination of the dose inside the phantom (the dose could be at points, lines, planes, or volumes within the phantom); and in-vivo dosimetry, which includes measurement or determination of the dose inside the patient (this can be performed invasively, i.e., inside the patient, or non-invasively, i.e., on or some distance from the patient, whereby the in-vivo dose at the point of interest is obtained by extrapolation).

Dose verification can be performed at different locations with different configurations of the dosimeter. When an electronic portal dose imager (EPID) is used as the dosimeter, the following dose verification options are available:

(a) non-transmission pre-treatment dosimetry: acquiring an image for each field without patient or phantom in the beam and:
  comparing acquired image (raw image or converted to dose distribution image) with predicted EPID response or predicted dose image (PDI) at the level of the imager (portal dosimetry); or
  comparing dose reconstructed inside the patient/phantom CT scan (convert image to energy fluence, use as input for dose calculation algorithm) with plan calculated with patient/phantom CT scan.

(b) non-transmission treatment dosimetry: acquiring image for each field with the detector located between source and patient during treatment and:
  comparing acquired image (raw image or converted to dose distribution image) with predicted EPID response or predicted dose image (PDI) at the level of the imager during treatment time (portal dosimetry); or
  comparing dose reconstructed inside the patient/phantom CT scan (convert treatment image to energy fluence, use as input for dose calculation algorithm) with plan calculated with patient/phantom CT scan.

(c) transmission treatment dosimetry: acquiring image for each field with the detector located behind the patient or phantom and:
  comparing acquired image (raw image or converted to dose distribution image) with predicted EPID response or predicted dose image (PDI) at the level of the imager, behind the patient/phantom (portal dosimetry); or
  comparing reconstructed dose inside the patient CT scan either back-project primary signal (using correction based algorithms) or convert image to energy fluence, use as input for dose calculation algorithm with plan calculated with patient CT scan.

In an exemplary embodiment, the pre-treatment dosimetric validation process includes delivering the radiation beam, absent the patient, onto the EPID 20 as per the treatment plan, measuring the delivered radiation dose, and comparing the measured dose with the predicted dose. The dose distribution may be verified by evaluating the dose distribution for a few significant points within the target volume, a grid of points over a 2D contour or image of the patient, or a 3D array of points that covers the patient's anatomy.

In operation, for each treatment beam, an EPID image is acquired during full radiation delivery with the radiation beams at the planned gantry angles $\theta$. The EPID 20 receives data from different projection angles $0 \le \theta \le 360°$ as the linear accelerator 2 rotates around the gantry 7. The EPID 20 collects the transmitted radiation from each segment. The various segments for a single beam are integrated, and a single 2D digital image per beam (i.e., per gantry angle) is generated. The raw 2D images are sent to the computer 40 for further processing. The EPID images can be captured in a continuous dosimetric fashion without syncing the beam pulses and the EPID readout in order to provide a plurality of raw 2D portal images (i.e., a fluoroscopic image sequence). The system 100 can further include a frame grabber card (not shown) and associated hardware and software tools (not shown) which allow the raw image frames to be directly exported from the EPID to the computer 40 before any correction is applied. The system 100 further includes a synching module configured to associate the acquired image frames with the treatment information (i.e., plan identification, plan parameters, etc.). Thus, during pre-treatment verification, 2D portal images (EPIs) are acquired using the electronic portal dose imaging device (EPID) 20 for each arc field segment in the absence of the patient. Each portal image (EPI) is measured under the same condition as the actual treatment, but without the patient placed in the beam.

Figure 3:
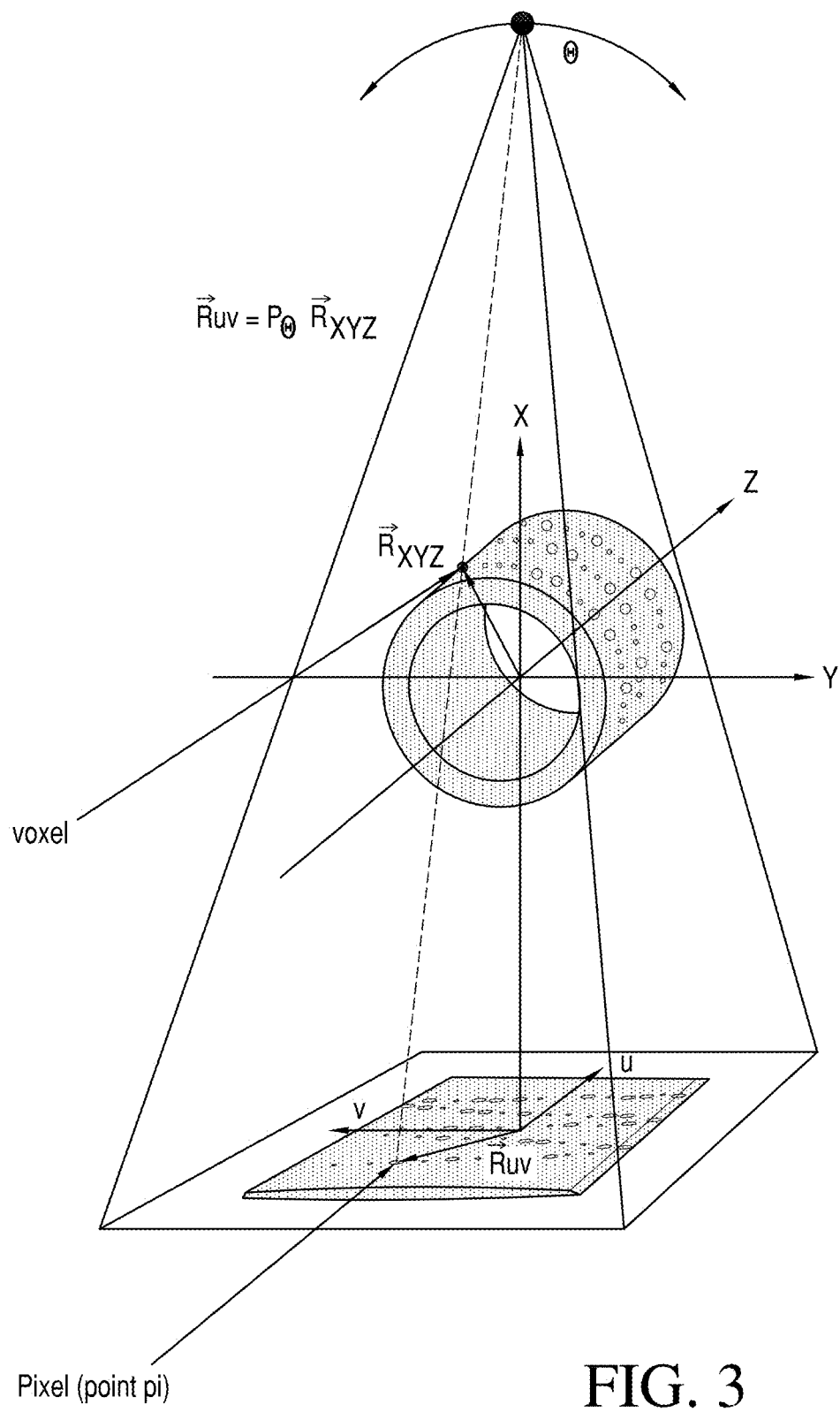
FIG. 3 illustrates a pixel-voxel relationship.

The acquired EPID images can be converted into 2D absolute dose images (PDIs) (i.e., portal dose images) using a dosimetric calibration model. Portal dose images (PDIs) represent absolute dose distributions at the plane of the EPID, and are obtained by converting gray scale pixel values to dose values or simulation of the gray scale pixel values. To convert portal images to portal dose images, any one of an empirical or simulation models can be used. In a first model, the EPID signal is converted to dose using a calibrated detector, such as, but not limited to, an ionization chamber inside water, or a mini-phantom, or film. The second approach simulates or models the detector response by Monte Carlo or other empirical simulation techniques. The conversion provides a unique pixel-voxel relationship, namely, a relationship between the dose at a particular voxel $R_{xyz}$ and the dose at a corresponding detector pixel or point $R_{pi}$. As shown in FIG. 3, each voxel in the patient volume is associated with a particular point $R_{pi}$ (i.e., pixel) in the EPID plane.

By continuously converting the measured EPID images into absolute portal dose images (PDIs), a sequence of measured absolute portal dose images is obtained. The sequence of measured absolute portal dose images can be integrated to generate a single 2D digital image per beam (i.e., per gantry angle). The generated 2D digital images can be stored in the computer processor 40. Since the plurality of measured portal dose images represents a series of image point locations/positions at different gantry angles $\theta$, the plurality of portal dose images can be stored as a data set mapped in an array having three-dimensional (3D) position information of the image points, with the beam delivery angle being one of the parameters. The predicted portal dose images can also be stored as a data set mapped in an array similar to the one used for storing the plurality of measured portal dose images.

Figure 4:
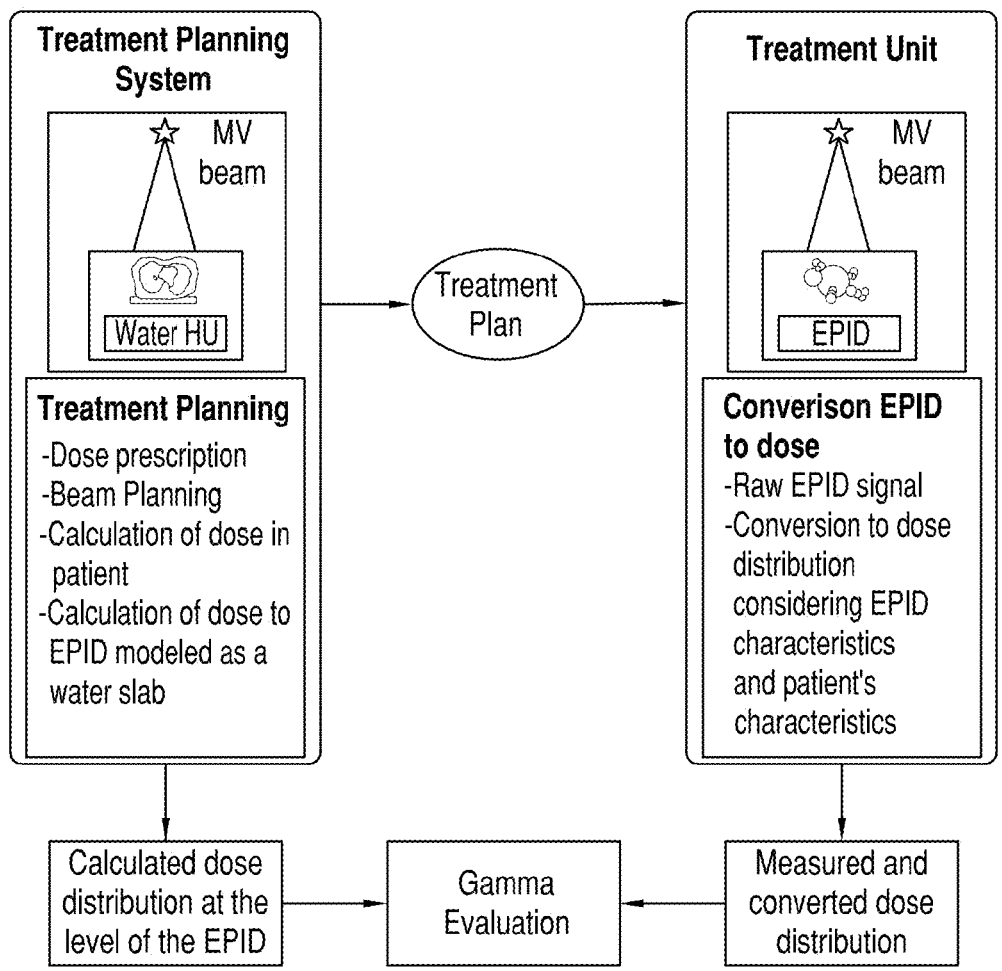
FIG. 4 illustrates a dose verification process according to various embodiments of the invention.

In order to determine the differences between the measured and the predicted doses as shown in FIG. 4, the treatment planning data and the measured portal dose images are first registered to a single coordinate system. This can be done using any available program, including MATLAB, for example, which allows for the viewing and the analysis of all treatment plans in a standard format. Then the measured dose recorded using the portal imager is registered with the CT image set. Dose profiles are next taken through the target volume in a plurality of orthogonal directions, and each profile is evaluated for shifts in the dose between the predicted and measured doses.

Dose differences can also be determined by evaluating dose distributions. A 3D dose distribution for each beam can be obtained by reconstructing the dose within the patient volume in multiple planes parallel to the EPID. The reconstruction can be done using any available reconstruction algorithms/models. The reconstruction models can include gantry angles as well as the position and the external contours of the patient as variables. In order to reconstruct the dose within the patient volume, the measured portal dose images are first converted to energy fluence, then the energy fluence is back-projected through the reconstruction volume, followed by the calculation of the 3D dose distribution delivered to the patient.

Figure 5:
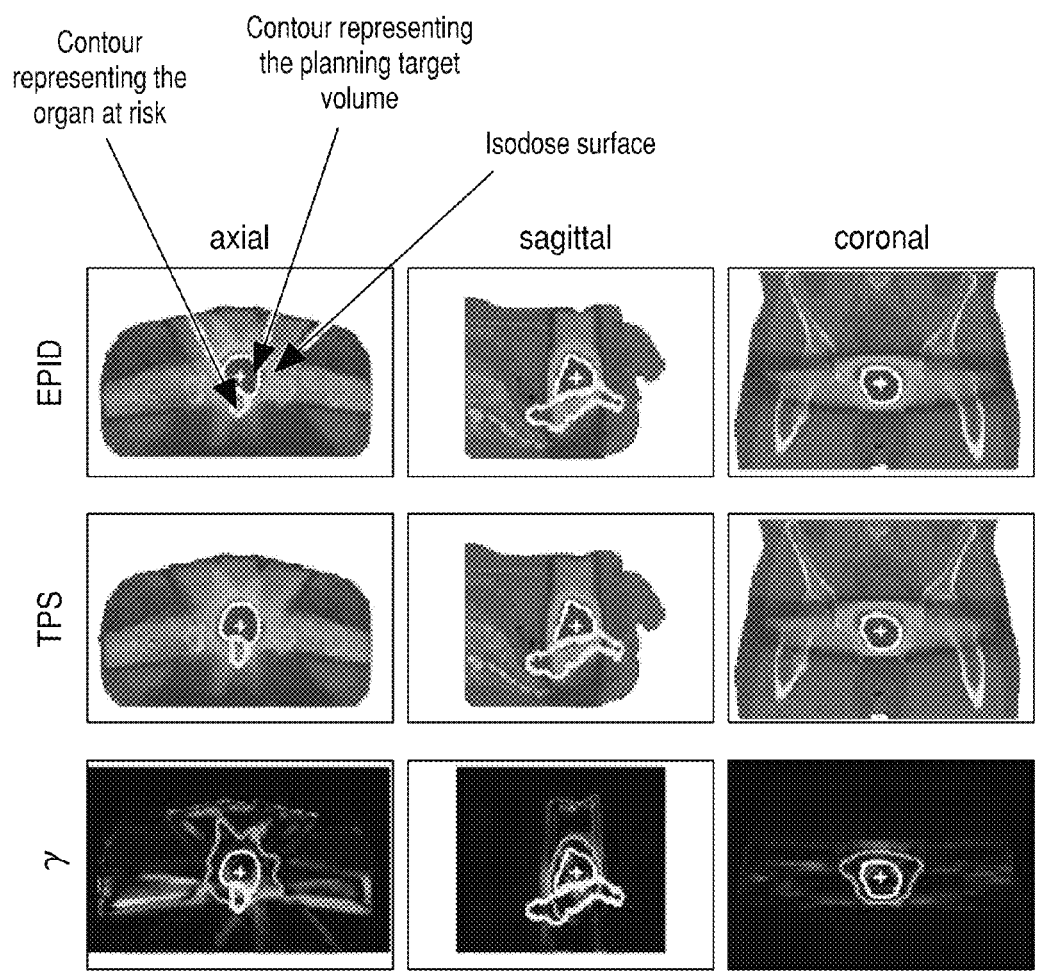
FIG. 5 illustrates a 3D dose distribution verification process and results according to various embodiments of the invention.

Gamma evaluation is a method generally used to quantitatively compare dose/dose distributions. The gamma method uses a comparison between a measured and predicted dose/dose distribution, as shown in FIGS. 4 and 5. FIG. 5, illustrates the 3D dose distribution reconstructed from EPID transmission images, the planned 3D dose distribution from the TPS, and the resulting 3D gamma distribution, through three orthogonal planes through the isocenter (white mark) with the dose distribution overlayed on the corresponding slices from the planning CT scan data.

Generally, the gamma evaluation method combines a dose difference criterion with a distance-to-agreement (DTA) criterion which makes it a suitable method for both low and high dose gradient regions. Dose distributions can be subdivided into regions of low and high dose gradients, each with a different acceptance criterion. High dose gradients could be regions defined as pixels with maximum relative dose differences above 10% for neighboring pixels, for example. In high dose gradient regions a small spatial error either in the calculation or the measurement results in a large dose difference between measurement and calculation. Dose difference in high dose gradient regions may therefore be unimportant, and the concept of distance-to-agreement (DTA) distribution is used to determine the acceptability of the dose calculation. The distance-to agreement (i.e., geometric) (DTA) criterion (i.e., parameter) is the distance between a measured data point and the nearest point in the predicted dose distribution that exhibits the same dose.

To determine dose variations using the gamma evaluation method, the relative dose difference between portal dose images (PDIs) is calculated by comparing each point in the measured dose image with the same point in the predicted dose image. The gamma evaluation method is a technique that unifies dose distribution comparisons using acceptance criteria. The measure of acceptability is the multidimensional distance between the measurement and predicted points in both the dose and the physical distance. The gamma value is a numerical quality index that serves as a measure of disagreement in the regions that fail the acceptance criteria and indicates the calculation quality in regions that pass. Gamma values below unity indicate agreement within the passing criteria. The passing criteria for dose difference criteria (DD) and the geometric (Distance to Agreement, DTA) criteria is generally 3% and 3 mm, respectively. The gamma value is calculated based on these criteria. Thus, for the conventional two component gamma function, a point is taken in the measured dose, and compared to all points in the predicted dose that fall within a geometrical search box defined by the (DTA). The point in the predicted dose with the lowest gamma index is considered the best match.

For two static 3D dose distributions, a dose which is predicted and is therefore labelled the referenced dose (or searched dose), and a measured dose which is labelled the compared dose, the gamma index ($\gamma$) can be obtained for a point $p_{com}$ in the compared dose via eq. 1:

$$\gamma(p_{com}) = \min\left\{\sqrt{\frac{d^2(p_{com}, sp_{ref})}{DTA^2} + \frac{\delta^2(p_{com}, sp_{ref})}{DD^2}}\right\} \forall \{sp_{ref} \in \tilde{v}\} \quad (1)$$

where $p_{com}$ is a fixed geometrical point of a voxel in the compared dose; $sp_{ref}$ is any point within the search sphere $\tilde{v}$ (whose radius=DTA) in the reference dose; and $d(p_{com}, sp_{ref})$, and $\delta(p_{com}, sp_{ref})$ are the geometrical distance and dose difference between points $p_{com}$ and $sp_{pred}$, respectively. The $\gamma$ index is calculated for each voxel in the search sphere $\tilde{u}$ and the lowest value kept as the $\gamma$ value for point $p_{com}$. The process is repeated for every voxel in the measured dose until a 3D gamma ($\gamma$) index with the same dimensions as the measured dose is produced.

In high gradient regions, gamma evaluation parameters $\Delta x$ and $\Delta y$ are used to determine displacement, where $\Delta x$ and $\Delta y$ are the spatial distances between the measured and the predicted dose points in horizontal and vertical directions, respectively. In low gradient regions, the doses are compared directly with an acceptance tolerance placed on the difference between the measured and calculated doses. A pixel is selected as low dose gradient if the maximum relative dose difference is below about 5% for all neighboring pixels. To determine dose variations, the relative dose difference between two PDIs is calculated by comparing each point in the measured dose distribution with the same point in the predicted dose distribution.

The gamma value or distance metric $\Gamma$ is a numerical quality index that serves as a measure of disagreement in the regions that fail the acceptance criteria and indicates the calculation quality in regions that pass. The passing criteria for dose difference criterion (DD) and the distance to agreement criterion (DTA) is generally 3% and 3 mm, respectively. The gamma value $\Gamma$ is calculated and compared with these criteria.

A general representation of the method for determining an acceptance criteria that considers both the dose difference and the distance criteria is as follows:

$$\Gamma(r_p, r_m) = \sqrt{\frac{r^2(r_p, r_m)}{DTA^2} + \frac{\delta^2(r_p, r_m)}{DD^2}} \quad (2)$$

where

-continued $$\Gamma(r_p, r_m) = \sqrt{\Delta x_{p-m}^2 + \Delta y_{p-m}^2} \text{ and} \quad (3)$$

$$\delta(r_p, r_m) = D_p(r_p) - D_m(r_m) \quad (4)$$

with r being the spatial distance between a predicted point $r_p$ in the predicted portal dose distribution and a corresponding measured point $r_m$ in the measured dose distribution; X and Y representing the spatial locations of the predicted and measured points $r_p$ and $r_m$ along the X and Y axis (i.e., horizontal and vertical directions) of the measurement plane, with $x_p$ and $x_m$ indicating the locations along the X axis of the predicted and measured points point $r_p$ and $r_m$, respectively, and $y_p$ and $y_m$ indicating the locations along the Y axis of the predicted and measured points $r_p$ and $r_m$, respectively; δ indicating the dosimetric difference, namely, the difference between the dose values on the predicted and measured distributions, with $D_p$ representing the predicted dose value and $D_m$ the measured dose value. The gamma value Γ is calculated for a specific predicted point in the measured image. The same predicted point is compared to other points in the measured image. For all points, a gamma value Γ is computed and the minimum of these values is the gamma index or gamma error value γ which belongs to the predicted point $r_p$:

$$\gamma(r_p) = \min\{\Gamma(r_m, r_p)\} \forall \{r_m\} \quad (5)$$

meaning that the gamma value is the minimum generalized gamma value Γ in the set of evaluated values. This calculation is done for all points in the predicted image. The gamma function γ is thus determined. The pass-fail criteria is then determined by the following:

$$\gamma(r_p) \leq 1, \text{ calculation passes} \quad (6)$$

$$\gamma(r_p) > 1, \text{ calculation fails} \quad (7)$$

This means that if the gamma index γ is less than or equal to one, that measured point is within the ellipsoid of acceptance and passes the criteria as acceptably agreeing with the calculated dose. The gamma index is then found at all points in the measured distribution and a percentage of points passing can be used to assess the overall agreement between the measured and predicted dose. Generally, if at least about 90%-98% of the evaluated points pass the single gamma criteria, namely, pass the 3% DD and the 3 mm DTA, for example, the dose delivered is said to be in agreement with the predicted dose, and the quality assurance measurement is accepted.

The shortcomings of evaluating all points with a single gamma criteria (i.e., applying the same DD and DTA passing values for all points, for example) is that each point, regardless of it representing dose intensity in a critical organ, a target, or a healthy tissue, is being evaluated the same. Thus, if the single gamma criteria is too loose, namely, the values for the dose DD and the distance-to-agreement DTA criteria are too high, points, and ultimately the treatment plan, could pass dose inspection (i.e., pass the gamma index) even though the existing dose discrepancy may be too much for a critical organ (the consequences of a hot spot generated in a critical organ are much more severe than for a hot spot in the target or a healthy tissue, for example). On the other hand, if the single gamma criteria is too stringent, namely, the values for the dose DD and the distance-to-agreement DTA criteria are too low, points, and ultimately the treatment plan, may not pass dose inspection, even though the detected dose discrepancy may not have any harmful effects on the patient. In such a case, the treatment plan may fail quality assurance even though the dose, if delivered according to plan, would not harm the patient.

Instead of using one single gamma criteria to evaluate the points in the measurement plane, in the present disclosure, a method is applied whereby different points are evaluated using different evaluation criterias. Therefore, some points could be evaluated using a stringent gamma criteria, and some points could be evaluated using a less stringent criteria. For example, points associated with critical organs could be evaluated using a more stringent gamma criteria than the gamma criteria used to evaluate points that are associated with the target or normal tissue. On the other hand, points associated with the target could be evaluated using a gamma criteria which is less stringent than the gamma criteria associated with the critical organ, but more stringent than the gamma criteria used to evaluate points associated with normal tissue.

Alternatively, the points associated with the target and the normal tissue could be evaluated using the same gamma criteria, which could be less stringent than the gamma criteria used for evaluating points associated with a critical organ.

Alternatively, the points associated with the critical organ and the target could be evaluated using the same gamma criteria, which is more stringent than the gamma criteria used for points that are associated with normal tissue.

In an alternative embodiment, each point could be evaluated using its own gamma criteria. Thus, each point could be evaluated using a corresponding gamma criteria. The gamma criterias could be different from each other.

In an alternative embodiment, the points associated with a critical organ could be evaluated using a first evaluation criteria, and points associated with a target could be evaluated using a second evaluation criteria, wherein the first evaluation criteria is based on a predetermined minimum absolute dose value and the second evaluation criteria is based on a predetermined maximum absolute dose value.

In an alternative embodiment, the points associated with a critical organ could be evaluated using a first evaluation criteria, points associated with a target could be evaluated using a second evaluation criteria, and points associated with a normal tissue could be evaluated based on a third evaluation criteria, wherein the first evaluation criteria is based on a predetermined minimum absolute dose value, the second evaluation criteria is based on a predetermined maximum absolute dose value, and the third evaluation criteria is based on an absolute dose value which is in between the maximum and minimum absolute dose values.

In an exemplary embodiment, an evaluation method is applied where points $r_{pi}$ in the measurement plane are evaluated using corresponding gamma criterias. Therefore, some points $r_{pi}$ in the dose distribution image could be evaluated using a first gamma criteria $\gamma_1$ where the passing error values are a % DD and bmm DTA, some points $r_{pi}$ could be evaluated using a second gamma criteria $\gamma_2$ where the passing error values are a'% DD and b'mm DTA, and some points $r_{pi}$ could be evaluated using a third gamma criteria $\gamma_3$ where the passing error values are a'''% DD and b''mm DTA, for example. The values a-a'' for the dose discrepancies can range between 2%-4%, for example, and the values b-b'' for the distance-to-agreement criteria could range between 2 mm-4 mm, for example. The number of different gamma criterias and the associated passing error values disclosed are only exemplary, and any number of different gamma criterias and any number of passing error value combinations can be used. Using different gamma criteria for different points in the measurement plane increases the flexibility of dose error evaluation, and thus increases the accuracy of critical hotspot detection (i.e., hotspots for which detection is far more critical than others).

Therefore, for each point $r_{pi}$, a gamma value $\Gamma_i$ is computed and the minimum of these values represents the gamma index or gamma error value $\gamma_i$ which belongs to a predicted point $r_{pi}$:

$$\gamma_i(r_{pi}) = \min\{\Gamma_i(r_{mi}, r_{pi})\} \forall \{r_{mi}\}, \quad (8)$$

where $$\Gamma_i(r_{pi}, r_{mi}) = \sqrt{\frac{r^2(r_{pi}, r_{mi})}{DTA_i^2} + \frac{\delta^2(r_{pi}, r_{mi})}{DD_i^2}} \quad (9)$$

$$\Gamma(r_{pi}, r_{mi}) = \sqrt{\Delta x_{pi-mi}^2 + \Delta y_{pi-mi}^2} \text{ and} \quad (10)$$

$$\delta(r_{pi}, r_{mi}) = D_p(r_{pi}) - D_m(r_{mi}) \quad (11)$$

with r being the spatial distance between a predicted point $r_{pi}$ in the predicted portal dose distribution and a corresponding measured point $r_{mi}$ in the measured dose distribution; X and Y representing the spatial locations of the predicted and measured points $r_{pi}$ and $r_{mi}$ along the X and Y axis (i.e., horizontal and vertical directions) of the measurement plane, with $x_{pi}$ and $x_{mi}$ indicating the locations along the X axis of the predicted and measured points point $r_{pi}$ and respectively, and $y_{pi}$ and $y_{mi}$ indicating the locations along the Y axis of the predicted and measured points $r_{pi}$ and respectively; $\delta$ indicating the dosimetric difference, namely, the difference between the dose values on the predicted and measured distributions, with $D_p$ representing the predicted dose value and $D_m$ the measured dose value. The gamma value $\Gamma_i$ is calculated for a specific predicted point $r_{pi}$ in the measured image and the pass-fail criteria is independently determined for each point $r_{pi}$ by the following:

$$\gamma_i(r_{pi}) \leq 1, \text{ calculation passes} \quad (12)$$

$$\gamma_i(r_{pi}) > 1, \text{calculation fails} \quad (13)$$

Because the gamma index $\gamma_i$ could be different for different points $r_{pi}$ in the measured distribution dose, each point $r_{pi}$ is evaluated based on a gamma criteria that is suitable for that particular point $r_{pi}$. The correspondence between each evaluated point $r_{pi}$ in the measured dose distribution image, the corresponding gamma criteria ($\gamma_i$), the corresponding passing criteria for dose difference criterion (DDi) and the corresponding distance to agreement criterion (DTAi) can thus be configured as follows:

TABLE 1

| Point ($r_{pi}$) | Gamma Criteria ($\gamma_i$) | Dose Difference Criteria ($DD_i$) | Distance to Agreement Criteria ($DTA_i$) |
|---|---|---|---|
| $r_{p1}$ | $\gamma_1$ | $DD_1$ | $DTA_1$ |
| $r_{p2}$ | $\gamma_2$ | $DD_2$ | $DTA_2$ |
| $r_{p3}$ | $\gamma_3$ | $DD_3$ | $DTA_3$ |
| $r_{p4}$ | $\gamma_4$ | $DD_4$ | $DTA_4$ |
| . | . | . | . |
| . | . | . | . |
| . | . | . | . |
| $r_{pi}$ | $\gamma_i$ | $DD_i$ | $DTA_i$ |

Therefore, each point in the measured dose distribution image is evaluated using its own gamma criteria ($\gamma_i$). Each gamma criteria ($\gamma_i$) has a specific dose difference criteria DDi and a specific distance to agreement criteria DTAi, so that each point ($r_{pi}$) can be evaluated independently based on a more stringent or more lenient passing criteria.

In an exemplary embodiment, different gamma criterias $\gamma_i$, and thus, different values for the associated dose difference $DD_i$ and the distance to agreement $DTA_i$, could be used to evaluate points $r_{pi}$ associated with different anatomical structures, such as the target (t), critical organs (co), and normal tissue (nt). As such, points $r_{pi}$ associated with a critical organ could be evaluated using a first gamma criteria ($\gamma_{co}$), points $r_{pi}$ associated with the target could be evaluated using a second gamma criteria ($\gamma_t$), and points $r_{pi}$ associated with healthy normal tissue could be evaluated using a third gamma criteria ($\gamma_{nt}$). Critical organs could include organs whose sensitivity to radiation is such that the dose received from a treatment plan may be significant compared to its tolerance. Critical organs could include organs that are immediately adjacent (close) to the target and also organs that although not immediately adjacent the target, have a very low tolerance dose. Examples of critical organs include, but are not limited to, spinal cord, heart, lung, orbits, parotid glands, eye lens, etc. The target includes the tumor to be irradiated, and normal tissue is healthy tissue surrounding the target and which is neither the target nor the critical organ.

The first gamma criteria ($\gamma_{co}$) could be more stringent than the second ($\gamma_t$) and third gamma criterias ($\gamma_{nt}$), and the second gamma criteria ($\gamma_t$) could be more stringent than the third gamma criteria ($\gamma_{nt}$). The dose difference criterion ($DTA_t$), and the corresponding distance to agreement criterion ($DTA_{co}$) associated with the first gamma criteria could be 2% and 2 mm, for example, the dose difference criterion ($DD_t$), and the corresponding distance to agreement criterion ($DTA_t$) associated with the second gamma criteria could be 3% and 3 mm, for example, and the dose difference criterion ($DD_{nt}$), and the corresponding distance to agreement criterion ($DTA_{nt}$) associated with the third gamma criteria could be 4% and 4 mm, for example. The values for the dose difference and corresponding distance to agreement criterions are exemplary only and any other applicable values and combination of values could be used.

Thus, points $r_{pi}$ in the measured dose distribution (i.e. pixels in the plane of the EPID) which are associated with points (voxels) of critical organs could be evaluated using the first gamma criteria ($\gamma_{co}$), the first gamma criteria being more suitable for assessing dose errors in critical organs, points $r_{pi}$ which are associated with points (voxels) of the target could be evaluated using a second gamma criteria ($\gamma_t$), which is more suitable for assessing dose errors in the target, and points $r_{pi}$ which are associated with points (voxels) of the normal tissue could be evaluated using a third gamma criteria ($\gamma_{nt}$), which is more suitable for assessing normal tissue. Because the gamma criteria used for assessing critical organs is more stringent than the gamma criteria used for assessing the target and the normal tissue, this evaluation method allows for a more accurate evaluation of the treatment dose delivery.

In order to associate points $r_{pi}$ in the measurement plane with points (voxels) of the different anatomical structures, three-dimensional points $R_{xyz}$ within the anatomical structure are projected onto the two-dimensional (2D) plane of the EPID (i.e., the measurement plane) using any applicable projection methods. By projecting the three dimensional (3D) points $R_{xyz}$ onto the measurement plane, each of the projected points $R_{xyz}$ will be associated with a corresponding point $r_{pi}$ within the measurement plane. The number of points $R_{xyz}$ to be projected onto the measurement plane is variable, and could include all or a portion of the points $R_{xyz}$ included in the anatomical structure.

Since a projected point $R_{xyz}$ represents a point associated with a target, an organ of interest, or a healthy tissue surrounding the target, the point $r_{pi}$ onto which a point $R_{xyz}$ projects will be evaluated using a gamma criteria associated with the respective anatomical structure. Thus, if a projected point $R_{xyz}$ is a point located within a critical organ, and point $R_{xyz}$ projects onto point $r_{pi}$, then point $r_{pi}$ will be evaluated using the gamma criteria ($\gamma_{co}$) associated with the critical organ. If the projected point $R_{xyz}$ is a point located within the target, and point $R_{xyz}$ projects onto point $r_{p2}$, then point $r_{p2}$ will be evaluated using the gamma criteria ($\gamma_t$), which is associated with the target. If, on the other hand, the projected point $R_{xyz}$ is a point located within a healthy normal tissue, and point $R_{xyz}$ projects onto $r_{p3}$, then point $r_{p3}$ will be evaluated using the gamma criteria ($\gamma_{nt}$) which is associated with the normal tissue.

If a plurality of points $R_{xyz}$ of the same anatomical structure project onto a plurality of points $r_{pi}$, then each of the plurality of those points $r_{pi}$ will be evaluated according to the gamma criteria associated with that particular structure. If, on the other hand, two or more points $R_{xyz}$ of different structures project onto a single point $r_{pi}$ in the measurement plane, and each structure is associated with its own gamma criteria, then point $r_{pi}$ will be evaluated using the gamma criteria which is the more stringent one between the applicable gamma criterias associated with the different anatomical structures projected onto that point.

Thus, the evaluation of dose distributions can be configured to be dependent on the particular structure that is being evaluated. The relationship between each evaluated point ($r_{pi}$) in the measured dose distribution image, the corresponding gamma criteria ($\gamma_i$), the corresponding passing criteria for dose difference criterion (DDi), and the corresponding distance to agreement criterion (DTAi) can be configured applied as illustrated in Table 2 below:

TABLE 2

| Point ($r_{pi}$) | Structure (critical organ (co), target (t), normal tissue (nt), etc.) ($A_i$) | Gamma Criteria ($\gamma_i$) | Dose Difference Criteria ($DD_i$) | Distance to Agreement Criteria ($DTA_i$) |
|---|---|---|---|---|
| $r_{p1}$ | $A_{co}$ | $\gamma_{co}$ | $DD_{co}$ | $DTA_{co}$ |
| $r_{p2}$ | $A_{co} + A_{nt}$ | $\gamma_{co}$ | $DD_{co}$ | $DTA_{co}$ |
| $r_{p3}$ | $A_{nt}$ | $\gamma_{nt}$ | $DD_{nt}$ | $DTA_{nt}$ |
| $r_{p4}$ | $A_t$ | $\gamma_t$ | $DD_t$ | $DTA_t$ |
| . | . | . | . | . |
| . | . | . | . | . |
| . | . | . | . | . |
| $r_{pi}$ | $A_i$ | $\gamma_i$ | $DD_i$ | $DTA_i$ |

The type of different anatomical structures disclosed are only exemplary, and any number of different structures and associated gamma criteria can be used.

In an alternative embodiment, each type of critical organ could be assigned its own separate gamma criteria. For example, if the critical organ is the spinal cord, its assigned gamma criteria could be different than the gamma criteria assigned to a different critical organ, such as a lung or heart, for example. In yet another embodiment, each type of target and/or type of normal tissue could also be assigned their own individual gamma criteria and associated dose and distance agreement values.

Figure 6:
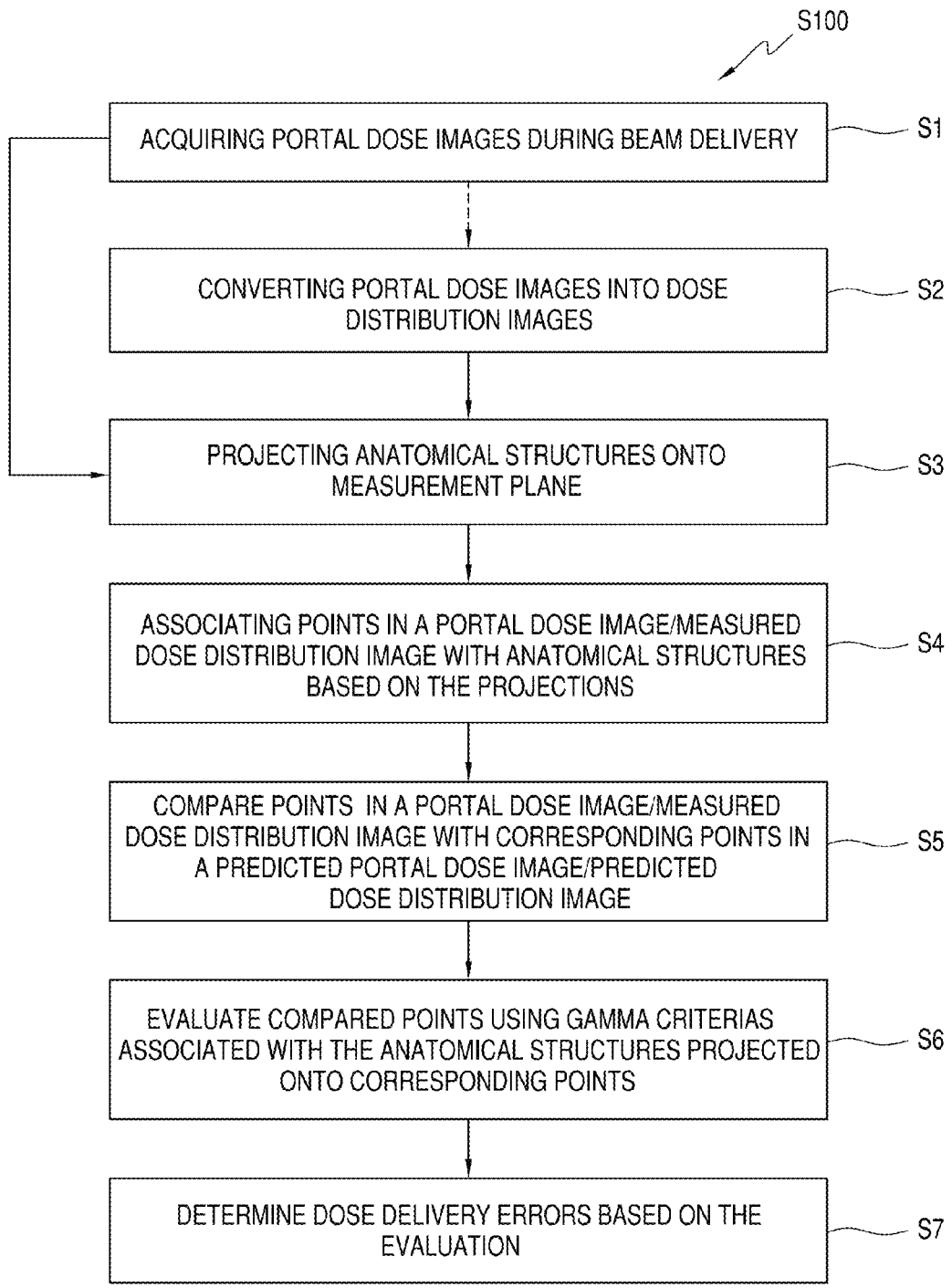
FIG. 6 is a flow chart illustrating a dose evaluation process using different gamma criterias according to various embodiments of the invention.

The information regarding the different gamma criterias used to evaluate different anatomical structures, such as critical organ, target, and healthy tissue can also be stored in a database of computer processor 40 for later use. The information stored in the database can later be used to automate the process of evaluation of dose distributions based on the particular structure that is being evaluated. In operation, a process S100 as shown in FIG. 6 can be applied for evaluating radiation dose delivery to a target volume. In step S1, portal dose images are acquired during treatment beam delivery according to a treatment plan, without the patient in place. Optionally, the portal dose images could be converted to radiation dose distribution images in S2 prior to evaluation. In step S3, points within the anatomical structures contained in the volume of interest shown in the pre-treatment images are projected onto the measurement plane. In step S4, each point in a measured dose distribution image is associated with an anatomical structure based on the projections. In step S5, the points in a dose distribution image are compared with associated points in a predicted dose distribution image. In step S6, each compared point is evaluated using a gamma criteria which is associated with the anatomical structure projected onto that point. In step S7, the dose delivery errors are determined based on the result of the evaluation.

Accordingly, using process S100, the radiation dose delivery to a target region can be evaluated by comparing the generated radiation dose distribution image with a corresponding predicted radiation dose distribution image, the comparing including comparing points in the generated radiation dose distribution image with corresponding points in the predicted radiation dose distribution image; determining spatial and dose differences between the compared points; evaluating the compared points using different gamma criterias; and determining whether dose delivery is acceptable based on a result of the evaluation.

The radiation dose delivery is determined to be acceptable if a predetermined number of points in the measured radiation dose distribution image pass their respective gamma criteria. The predetermined number of points can range between about 90-100% of the total amount of evaluated points in the measured radiation dose distribution image. If the radiation dose delivery is determined to be acceptable, the radiation treatment proceeds to the next field. If not, the radiation treatment is stopped. The reason for the failure is further verified and adjusted, prior to the radiation treatment proceeding to the next field.

In an alternative embodiment, the radiation dose delivery is determined to be unacceptable if a predetermined number of points in the generated radiation dose distribution image which are associated with one or more critical organs fail to pass the critical organ gamma criteria. The predetermined number of points could be a range between 1-10% of the total number of points associated with critical organs. If the comparisons pass the predefined tolerance value, the treatment proceeds to the next field. If not, the treatment is stopped and the reson for the mismatch is verified. Alternatively, To reduce the calculation time, the gamma function can be applied on a graphics processing unit (GPU) as well as a central processing unit (CPU).

The above-described evaluation method could also be used for in-treatment dose verification. For in-treatment dose verification, i.e., for the actual treatment delivery with the patient 5 in place, the portal dose imaging device 30 can be positioned such that the detector 4 and the therapeutic radiation source 3 are arranged to be directly opposite from each other, and so that the detector 4 can continuously receive during the treatment the therapeutic radiation beams that pass through the target region of the patient 5. The portal dose imaging device (EPID) 30 then allows for the detecting and recording the transmission of the therapeutic beams from the source 3 that passes through the patient 5.

In operation, for each treatment beam, an EPID image is acquired during full radiation delivery with the radiation beams at the planned gantry angles θ. The EPID 20 receives data from different projection angles 0≤θ≤360° as the linear accelerator 2 rotates around the gantry 7. The EPID 20 collects the transmitted radiation from each segment. The various segments for a single beam are integrated, and a single 2D digital image per beam (i.e., per gantry angle) is generated. The raw 2D images are sent to the computer 40 for further processing. Each portal image (EPI) is generated under the same condition as is planned for the actual treatment. The EPID images can be captured in a continuous dosimetric fashion without syncing the beam pulses and the EPID readout in order to provide a plurality of raw 2D portal images. These portal images can be used to visualize the organ to be treated and to verify dose delivery. These images could also be integrated as well as converted into dose distribution images as described in detail throughout this disclosure. The treatment verification focuses on comparing of all or part of the planned and the delivered dose distribution based on measurements acquired during treatment of the patient. These measurements can then be used to determine the dose delivered to the detector or patient, or incident energy fluence obtained from measurements, as described in detail throughout this disclosure.

To determine whether the measured radiation dose is different from the expected radiation dose, during radiation treatment, points $r_{pi}$ within the portal dose images (PDIs) or within the dose distribution images are evaluated using a gamma evaluation method as described in detail throughout this disclosure.

Figure 7:
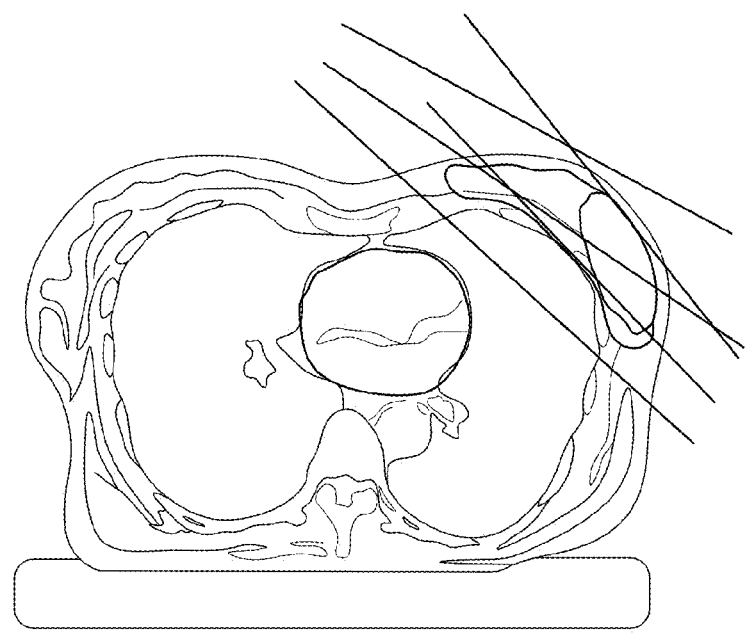
FIG. 7 illustrates tangential and surface beams irradiating a patient surface.

To decrease the time required to evaluate the dose distribution, and/or to eliminate false positives (i.e., falsely concluding that there is a discrepancy between the measured and the predicted dose in the patient), alternatively or in addition to the above described dose evaluation method using different gamma criterias, a method can also be applied whereby certain points $r_{pi}$ are excluded from being evaluated. The exclusion could be automatic. The points to be excluded from evaluation could be, but are not limited to, the points that are irradiated by radiation beams that travel near the surface of the patient and/or points that are irradiated by beams that do not intersect the patient, as shown in FIG. 7.

The exclusion of certain points from evaluation is justified because in situations where the radiation beams are tangential to the patient, a small change in the patient outline has the potential of introducing large changes in the measured dose, even though the actual dose delivered to the patient has not been significantly affected. In such a case, during dose evaluation, a large difference can be registered between the measured dose and the predicted dose. A false large dose difference may trigger an unnecessary stopping of the radiation treatment.

Further, dose measurement for beams that travel near the surface of the patient and beams that penetrate the skin at a depth of about 1 cm generally relate to skin dose or surface dose. Skin dose, however, is a limiting factor in radiation therapy treatments, and it is fairly common cause of interruptions in radiation therapy treatments. Skin dose is of particular concern when IMRT therapy is used to treat head and neck cancer, because the head and neck immobilization devices increases skin dose and the use of multiple tangential beams (which are common in IMRT treatments) can also increase it. The chosen planning and optimization strategy can also affect skin dose because, during the therapy planning process, the planning target volume sometimes is expanded to include the skin. When the planning target volume is expanded to include the skin, the skin dose is increased. On the other hand, when the skin is defined as a sensitive structure within the target volume, the skin dose is reduced. Because of such unpredictability in the skin dose measurements, the dose distributions to the surface and a few millimeters below the surface of the patient (i.e., below the skin), have been underestimated by about 15% during treatment planning, and therefore, dose distribution comparisons may give false information about the actual dose delivered to the patient.

Knowledge of skin dose would be beneficial in a range of treatments if it could be measured accurately and within acceptable workflow of patient throughput for fractionated therapy. However, many factors, such as beam types, beam energy, field size, beam modification devices, angle of incidence, complexities and deformations of the patient's surface profiles and heterogeneities of the interval tissue lead to the difficulty in achieving accurate surface dosimetry estimates or measurements. Irregular surface profiles of the treatment region decrease the accuracy of superficial dose prediction and may result in under-dosing or over-dosing in the delivered dose for specific treatment plans. Some of the available surface dosimetry methods have been proven to be able to measure superficial dose. However, these techniques require clinical intervention and additional personnel time for use, and each are limited by small fixed region measurements and sensitivity is often a function of angular orientation of the detector with respect to the incident beam. Some other detection methods have longer offline processing procedures which prevent superficial dose monitoring in real-time.

Since most of the surface dose measurements are inaccurate, in order to reduce false alarms, in the present disclosure, points $r_{pi}$ that are irradiated with beams that travel near the surface of the patient and/or beams that penetrate the skin at a depth of about 1 cm are excluded from evaluation. As such, points that would give rise to false positives are not considered in the dose distribution evaluation. This selective exclusion of evaluation points based on the patient surface information allows for real-time or near-real time verification of radiation treatment. Further, in order to reduce and/or eliminate false alarms, points that are irradiated with beams that do not intersect the patient can also be excluded from being evaluated for dose discrepancies.

In an exemplary embodiment, selective exclusion of points $r_{pi}$ based on beam irradiation and patient surface information can be done by excluding points $r_{pi}$ in the measured portal dose images which correspond to points $r_{pm}$ in the predicted portal images that are irradiated with beams that do not intersect the patients and/or beams that irradiate only the surface of the patient (or a depth of about 1 cm). The points $r_{pm}$ in the predicted portal images that are irradiated with beams that do not intersect the patients and/or beams that irradiate the surface of the patient and/or beams that irradiate the patient within about 1 cm below the surface of the skin can be determined during treatment planning by first generating either 3D voxelized volume (i.e., a 3D array of points that covers the patient's anatomy) from the previously obtained CT scan or a 2D voxelized region (i.e., a grid of points over a 2D contour or image of the patient) and drawing a grid of the pencil beams from the radiation source to one grid point in the beam's eye views (BEVs) plane within the field range. Beam's eye views are projections of the treatment beam axis, field limits, and outlined structures through the patient on to a corresponding virtual detector plane. Then each pencil beam can be traced to determine its interaction with the surface of the patient anatomy. From this, the radiation beams which do not intersect the patient and radiation beams that travel near the surface of the patient (i.e., within approximately 1 cm depth) can be traced to corresponding voxels in the 3D volume or 2D contour. Since each voxel can be associated with a corresponding pixel ($r_{pm}$) in the imager plane, the points $r_{pm}$ in the predicted dose images which are irradiated with beams that do not intersect the patient and beams that travel near the surface of the patient (i.e., within approximately 1 cm depth) can be determined and the information stored.

During dose evaluation, the points $r_{pi}$ in the measured portal dose images corresponding to points $r_{pm}$ in the predicted portal dose images which are irradiated with beams that do not intersect the patient and/or beams that travel only near the surface of the patient (i.e., within approximately 1 cm below the skin surface) are excluded from being evaluated for dose discrepancies. The rest of the points $r_{pi}$ in the measured portal dose images can be evaluated for dose discrepancies using a single gamma criteria based or multiple gamma criterias-based evaluation method, as described throughout this disclosure, for example. Excluding points from evaluation based on information about the patient surface effectively eliminates points that would otherwise give false positives in the dose error measurement.

In an alternative embodiment, the exclusion of points from evaluation can be done based on the beam angle of irradiation. For example, radiation beams which do not intersect the patient and radiation beams that travel near the surface of the patient (i.e., within approximately 1 cm below the skin surface) can be traced to corresponding voxels in the 2D contour of the patient or the 3D volume during preplanning. The irradiation beam angles for these voxels can be recorded and stored in a 3D array including voxel geometric position and beam angle as the parameters.

During dose evaluation, the points $r_{pi}$ in the measured portal dose images which are irradiated by beams at the same beam angles that were recorded as being beam angles for which the radiation beams do not intersect the patient and/or radiation beams that travel only near the surface of the patient (i.e., within approximately 1 cm depth) can be excluded from evaluation.

Figure 8:
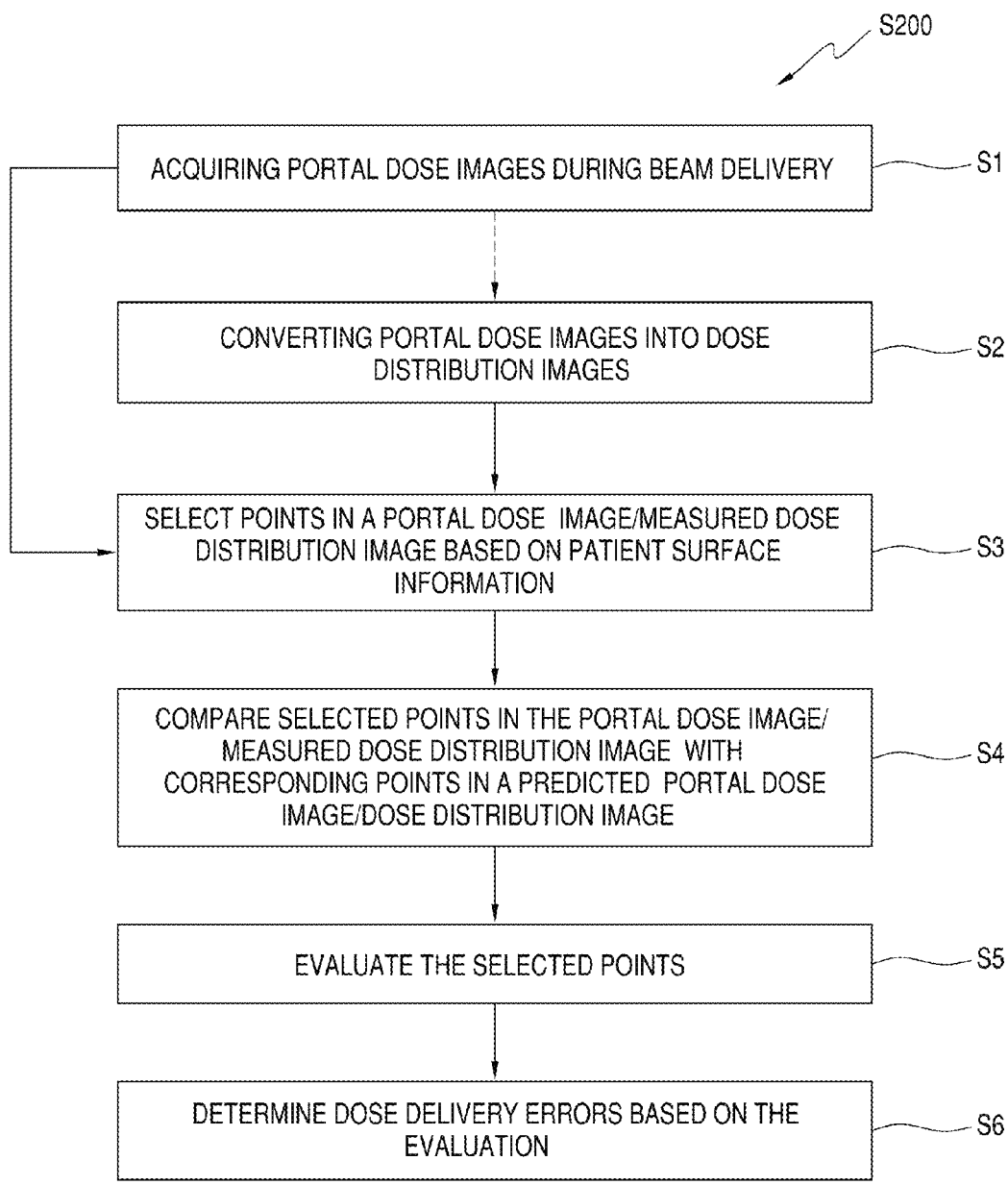
FIG. 8 is a flow chart of a selective dose evaluation method according to various embodiments of the invention.

Thus, for real-time dose evaluation, a process S200 as shown in FIG. 8 can be used wherein the points to be evaluated for dose discrepancies are selected based on patient surface information. In step S1 of process S200, a plurality of portal images are acquired during treatment beam delivery according to a treatment plan. Optionally, the portal dose images can be converted to radiation dose distribution images in S2. In step S3, points in a portal dose image, or if converted, in a dose distribution image, are selected for dose evaluation based on the patient surface. During the selection, points that are determined to be irradiated by beams that are not intersecting the patient and/or beams which travel only on the surface or within approximately 1 cm below the surface of the skin of the patient are excluded from the evaluation. The selected points, namely, the points which are not excluded, are then evaluated in step S4 by comparing the selected points in the portal dose image/measured dose distribution image with corresponding points in the predicted portal dose image/predicted dose distribution image. The selected points are then evaluated in step S5 using an evaluation method including, but not limited to, a gamma evaluation method. The gamma evaluation method could be a conventional gamma evaluation method where a single gamma criteria is used for all evaluated points, or a gamma evaluation method where each selected point is evaluated using its own gamma criteria, as described in detail throughout the disclosure. In step S6 the dose delivery is assessed based on the evaluation. The treatment is continued if a predetermined number of evaluated selected points pass the evaluation. The predetermined number could be at least 90-98% of the total number of evaluated points, for example. The treatment is stopped if a predetermined number of the evaluated selected points fail their evaluation. The predetermined number could be about 1-10% of the total number of evaluated selected points, for example. Thus, if the comparisons pass the predefined tolerance value, the treatment proceeds to the next field. If not, the treatment is automatically stopped and the reason for the mismatch is verified. Alternatively, if the comparison does not pass the predefined tolerance value, an alarm signal could be generated to alert the medical personnel of a radiation dose that is either too high, too low, or is not directed to the correct location within the patient. Based on the alarm signal, the medical personnel can stop the radiation treatment. The alarm signal can be a visible, audible, or any other alarm signal.

A database containing patient OAR, patient target geometry, patient surface information, as well as patient structure information (i.e., target, healthy tissue, critical organ), and the associated treatment plan and evaluation criterias, can also be generated and be used later for comparing the geometric configurations of the OARs and targets of a new patient with those of prior patients, whose plans are maintained in a database. Thus the database forms the basis of knowledge-based planning process, where the database of prior patients is built to serve as an external reference. As such, at the conclusion of a new plan, planners can search through the database and identify related patients by comparing the OAR target geometric relationships of the new patient with those of prior patients. The treatment plans of these related patients are retrieved from the database and guide planners in determining the doses delivered to the OARs in the new plan. The treatment plans of these related patients retrieved from the database are also used to determine feasible gamma criterias to be used for dose distribution evaluation, as well as proper evaluation points to be selected for evaluation. An internally developed algorithm, such as the RapidPlan™ knowledged-based software (developed by Varian Medical Systems Inc.), or any other available matching algorithms can be used to match cases from the database with new cases. Such algorithms make it possible to extract knowledge from past clinical experience and use it to generate mathematical models that expedite the creation of new treatment plans. The mathematical knowledge models greatly reduce the need for current time-consuming, manual trial-and-error processes by providing treatment planners with goals that are achievable for a specific patient's anatomy.

A user interface can also be included in the system for visualizing and analyzing data from both new and matched cases, including 3D CT scans, 2D images, hand-drawn slice contours, volume rendered structure maps, histograms of radiation dosages, radiation fluence maps, evaluation criterias, and selected evaluation points.

A non-transitory computer readable medium can be used to store the software or programmed instructions and data which when executed by a computer processing system 40 causes the system to perform various methods of the present invention, as discussed herein. The executable software and data may be stored in various places, including, for example, the memory and storage of the computer processing system 40 or any other device that is capable of storing software and/or data.

Accordingly, embodiments of quality control systems, methods and computer program products for selective evaluation of measurement points and use of different evaluation criteria for different measurement points have been disclosed.

Further, methods for evaluating radiation dose delivery to a target volume are disclosed, comprising: generating a radiation dose distribution image based on radiation delivered according to a treatment plan; comparing the generated radiation dose distribution image with a corresponding predicted radiation dose distribution image, the comparing including comparing points in the generated radiation dose distribution image with corresponding points in the predicted radiation dose distribution image; evaluating the compared points using different evaluation criteria; and determining whether dose delivery is acceptable based on a result of the evaluation.

Further, methods for evaluating radiation dose delivery to a target volume are disclosed, comprising: generating a radiation dose distribution image based on radiation delivered according to a treatment plan; projecting anatomical structures onto a measurement plane, the anatomical structures being associated with different gamma criterias; associating points in the generated distribution image with gamma criterias based on the projections; comparing points in the generated radiation dose distribution image with corresponding points in the predicted radiation dose distribution image; evaluating the compared points using gamma indexes based on the associating; and determining whether dose delivery is acceptable based on a result of the evaluation.

Further, methods for evaluating radiation dose delivery to a target are disclosed, comprising: generating a radiation dose distribution image based on radiation delivered according to a treatment plan; comparing the generated radiation dose distribution image with a corresponding predicted radiation dose distribution image; the comparing including comparing selected points in the generated radiation dose distribution image with corresponding points in the predicted radiation dose distribution image; evaluating the compared selected points; and determining whether dose delivery is acceptable based on a result of the evaluation, wherein the selected points include points selected based on patient surface information.

Further, systems for verifying radiation dose delivery in an arc-based radiation therapy device are disclosed, comprising: a portal imaging device configured to measure incident radiation dose from predetermined radiation fields and to generate portal dose images; and a processing device operably connected to the portal dose imaging device and being configured to store the measured portal dose images in a first array having spatial and angular locations of the delivered beams as dimensions, the processing device being further configured to store a plurality of predicted portal dose images in a second array having spatial and angular locations of the predicted beams as dimensions; the processing device being further configured to selectively compare points in the first array with corresponding points in the second array, wherein the selectively comparing includes excluding points based on patient surface information from the comparison, and wherein errors in the quantities of interest are determined based on the comparison.

Many alternatives, modifications, and variations are enabled by the present disclosure. Features of the disclosed embodiments can be combined, rearranged, omitted, etc. within the scope of the invention to produce additional embodiments.

Furthermore, certain features of the disclosed embodiments may sometime be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents.

What is claimed is:

1. A method for evaluating radiation dose delivery to a target, comprising:
   generating a radiation dose distribution image based on radiation delivered according to a treatment plan, the generated radiation dose distribution image including at least a first point and a second point;
   comparing the generated radiation dose distribution image with a corresponding predicted radiation dose distribution image, the comparing including comparing points in the generated radiation dose distribution image with corresponding points in the predicted radiation dose distribution image;
   evaluating the compared points using different evaluation criterias;
   and
   determining whether dose delivery is acceptable based on a result of the evaluation,
   wherein the evaluating includes evaluating the first point using a first gamma criteria including dose and spatial differences and evaluating the second point using a second gamma criteria including dose and spatial differences, the second gamma criteria being different than the first gamma criteria, or evaluating the first point against a maximum absolute dose value and the second point against a minimum absolute dose value.

2. The method of claim 1, wherein the evaluating includes evaluating dose and spatial differences between the generated and predicted points.

3. The method of claim 1, wherein the radiation dose delivery is determined to be acceptable if a predetermined number of points in the generated radiation dose distribution image pass their respective gamma criteria.

4. The method of claim 3, wherein the predetermined number of points is at least 90% of the total amount of evaluated points in the generated radiation dose distribution image.

5. The method of claim 1, wherein the first point is associated with the target and the second point is associated with an organ at risk.

6. The method of claim 5, wherein the second gamma criteria is more stringent than the first gamma criteria.

7. The method of claim 1, wherein each point in the generated radiation dose distribution image is associated with a respective gamma criteria.

8. The method of claim 7, wherein each gamma criteria includes a first parameter and a second parameter.

9. The method of claim 8, wherein the first parameter is associated with an acceptable dose difference, and the second parameter is associated with an acceptable spatial difference.

10. The method of claim 9, wherein the first parameter includes a range of between 2% and 4% and the second parameter includes a range of between 2 mm and 4 mm.

11. The method of claim 7, wherein the gamma criteria used for a point is dependent on an anatomical structure that is projected onto the point.

12. The method of claim 11, wherein if an anatomical structure is projected onto a plurality of points in the generated radiation dose distribution image, the plurality of points are evaluated using a first gamma criteria.

13. The method of claim 11, wherein if two anatomical structures are projected onto a single point in the generated dose distribution image, the point is evaluated using a gamma criteria which is the more stringent one between a first gamma criteria associated with a first anatomical structure and a second gamma criteria associated with a second anatomical structure.

14. The method of claim 13, wherein the anatomical structure includes organs, the target, and normal tissues.

15. The method of claim 14, wherein the organs include organs located adjacent the target.

16. The method of claim 14, wherein the organ includes a critical organ.

17. The method of claim 16, wherein the critical organ includes at least a portion of one of the following: spine, spinal cord, heart, brain, bladder, rectum, lung, heart, liver, stomach, kidney, pancreas, and eye.

18. The method of claim 1, wherein the portal dose images are obtained using an electronic portal dose imaging device (EPID).

19. The method of claim 18, wherein the electronic portal dose imaging device (EPID) is calibrated for measuring absolute dose.

20. The method of claim 19, wherein the measured dose is an absolute dose.

21. The method of claim 19, wherein the absolute dose calibration includes an absolute (EPID) conversion model.

22. The method of claim 1, further comprising generating an alarm signal and/or stopping radiation dose delivery to the target when dose delivery is unacceptable.

23. A method for evaluating radiation dose delivery to a target, comprising:
generating a radiation dose distribution image based on radiation delivered according to a treatment plan;
projecting anatomical structures onto a measurement plane, the anatomical structures being associated with different gamma criterias;
associating points in the generated distribution image with gamma criterias based on the projections;
comparing points in the generated radiation dose distribution image with corresponding points in the predicted radiation dose distribution image;
evaluating the compared points using gamma criterias based on the associating; and
determining whether dose delivery is acceptable based on a result of the evaluation.

24. The method of claim 23, wherein the evaluating includes evaluating dose and spatial differences between the generated and predicted points.

25. The method of claim 23, wherein the evaluating includes evaluating using a gamma evaluation method.

26. The method of claim 23, wherein the radiation dose delivery is determined to be acceptable if a predetermined number of points in the generated radiation dose distribution image pass their respective gamma criterias.

27. A method for selectively evaluating radiation dose delivery to a target, comprising:
generating a radiation dose distribution image based on radiation delivered according to a treatment plan;
comparing the generated radiation dose distribution image with a corresponding predicted radiation dose distribution image;
the comparing including comparing selected points in the generated radiation dose distribution image with corresponding points in the predicted radiation dose distribution image;
evaluating the compared selected points; and
determining whether dose delivery is acceptable based on a result of the evaluation,
wherein the selected points include points selected based on patient surface information.

28. The method of claim 27, wherein the selected points exclude points that are irradiated with beams that do not intersect the surface of the patient.

29. The method of claim 27, wherein the selected points exclude points that are irradiated with beams that intersect the patient at a predetermined distance below the surface of the patient.

30. The method of claim 29, wherein the predetermined distance includes a distance that is less than about 1 cm.

31. The method of claim 27, wherein the evaluating includes evaluating using a gamma evaluation method.

32. The method of claim 27, wherein the comparing includes comparing dose and spatial discrepancies between the selected points in the generated portal dose image and the predicted portal dose image.

33. The method of claim 27, wherein the evaluation is in real-time.

34. The method of claim 27, wherein the portal dose images are obtained using an electronic portal dose imaging device (EPID).

35. The method of claim 34, wherein the electronic portal dose imaging device (EPID) is calibrated for measuring absolute dose.

36. The method of claim 35, wherein the measured dose is an absolute dose.

37. The method of claim 35, wherein the absolute dose calibration includes an absolute (EPID) conversion model.

38. The method of claim 27, wherein the evaluating includes evaluating using different gamma criterias for different selected points.

39. The method of claim 27, wherein the radiation dose delivery is determined to be acceptable if a predetermined number of selected points in the generated radiation dose distribution image pass a gamma criteria.

40. The method of claim 39, wherein the predetermined number of points is at least 90% of the total amount of evaluated selected points in the generated radiation dose distribution image.

41. A system for verifying radiation dose delivery in an arc-based radiation therapy device, comprising:
a portal imaging device configured to measure incident radiation dose from predetermined radiation fields and to generate portal dose images; and
a processing device operably connected to the portal dose imaging device and being configured to store the measured portal dose images in a first array having spatial and angular locations of the delivered beams as dimensions, the processing device being further configured to store a plurality of predicted portal dose images in a second array having spatial and angular locations of the predicted beams as dimensions;

the processing device being further configured to selectively compare points in the first array with corresponding points in the second array, wherein the selectively comparing includes excluding points based on patient surface information from the comparison, and wherein errors in the quantities of interest are determined based on the comparison.

42. The system of claim 41, wherein the excluded points include points that are irradiated by beams that do not intersect the patient surface.

43. The system of claim 41, wherein the excluded points include points that are irradiated by beams that intersect the patient surface at a distance of less than about 1 cm below the patient surface.

44. The system of claim 41, wherein the excluded points include points that are irradiated by beams at predetermined angles.

45. The system of claim 44, wherein the predetermined angles are angles at which the beams do not intersect the patient surface and/or intersect the patient surface at a distance within about 1 cm below the patient surface.

* * * * *